United States Patent
Lee et al.

(10) Patent No.: US 9,232,923 B2
(45) Date of Patent: Jan. 12, 2016

(54) X-RAY IMAGING APPARATUS AND X-RAY IMAGE PROCESSING METHOD

(71) Applicant: SAMSUNG ELECTRONICS CO., LTD., Suwon-si (KR)

(72) Inventors: Jae Hak Lee, Yongin-si (KR); Young Hun Sung, Hwaseong-si (KR); Kang Eui Lee, Seoul (KR); Jong Ha Lee, Hwaseong-si (KR); Kwang Eun Jang, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 210 days.

(21) Appl. No.: 14/132,935

(22) Filed: Dec. 18, 2013

(65) Prior Publication Data

US 2014/0185738 A1    Jul. 3, 2014

(30) Foreign Application Priority Data

Dec. 28, 2012  (KR) .......................... 10-2012-0156254

(51) Int. Cl.
*A61B 6/00* (2006.01)
*A61B 6/02* (2006.01)

(52) U.S. Cl.
CPC .............. *A61B 6/022* (2013.01); *A61B 6/025* (2013.01); *A61B 6/027* (2013.01); *A61B 6/5205* (2013.01)

(58) Field of Classification Search
CPC ...... A61B 6/022; A61B 6/025; A61B 6/4241; A61B 6/461; A61B 6/482; A61B 6/5205; A61B 6/032; G01N 23/04
See application file for complete search history.

(56) References Cited

U.S. PATENT DOCUMENTS

2008/0267484 A1*  10/2008  Chen ..................... A61B 6/032
                                                    382/132
2012/0051613 A1    3/2012  Kamiya et al.

FOREIGN PATENT DOCUMENTS

| JP | 2003325499 A   | 11/2003 |
| JP | 2007229201 A   | 9/2007  |
| JP | 2010234003 A   | 10/2010 |
| KR | 1020110063659 A | 6/2011  |

* cited by examiner

*Primary Examiner* — Courtney Thomas
(74) *Attorney, Agent, or Firm* — Sughrue Mion, PLLC

(57) ABSTRACT

Disclosed herein is an X-ray imaging apparatus. The X-ray imaging apparatus includes at least one X-ray emitter which is configured to irradiate an object with X-rays at a plurality of X-ray emission positions, an X-ray detector which is configured to detect X-rays which are emitted by the X-ray emitter and to convert the detected X-rays into an electric signal, and an image processor which is configured to acquire a plurality of original X-ray images which respectively correspond to the X-ray emission positions from the generated electric signal and to estimate a virtual X-ray image which is acquirable at an X-ray emission position located between at least two of the plurality of X-ray emission positions, based on at least two of the original X-ray images.

20 Claims, 27 Drawing Sheets

X-RAY IMAGING APPARATUS AND X-RAY IMAGE PROCESSING METHOD

CROSS-REFERENCE TO RELATED APPLICATION(S)

This application claims priority from Korean Patent Application No. 10-2012-0156254, filed on Dec. 28, 2012 in the Korean Intellectual Property Office, the disclosure of which is incorporated herein by reference in its entirety.

BACKGROUND

1. Field

Exemplary embodiments relate to an X-ray imaging apparatus and an X-ray image processing method.

2. Description of the Related Art

X-ray imaging apparatuses are devices which may be used to visually identify, diagnose and detect matter, tissues, and structures inside an object, such as the human body and animals, or substances inside various luggage cases using X-rays (also referred to as Roentgen rays). For example, an X-ray imaging apparatus may be used to detect abnormal tissues, such as lesions or abnormal materials, inside a human body, to identify an inner structure of an object or components, or to scan luggage in an airport or the like.

In particular, an X-ray imaging apparatus emits X-rays toward an object, such as a human body or the like that is placed on a support table or at a predetermined position, from a predetermined direction, e.g., from a upward direction or a lateral direction, detects the emitted X-rays, and generates an X-ray image based on the detected X-rays, in order to identify the inside of the object.

An X-ray imaging apparatus uses, when a predetermined object is irradiated with X-rays, absorption or transmission characteristics of the X-rays with respect to matter based on properties of the matter through which the X-rays pass, e.g., density or the like.

Examples of the X-ray imaging apparatus include general X-ray imaging apparatuses and computed tomography (CT) and full field digital mammography (FFDM) apparatuses that acquire an image by using various kinds of X-rays.

Among these X-ray imaging apparatuses, an FFDM apparatus captures an image of the female breast and detects lesions, such as cancerous tissues, inside the breast. The FFDM apparatus also acquires an X-ray image by irradiating a female breast with X-rays and detecting X-rays which have propagated through the breast. A process of performing X-ray imaging of a breast by using the FFDM apparatus will now be described in detail. The breast is placed on a support plate, an upper surface of which is flat, and the breast is compressed by using the support plate and a compressor, thereby increasing an area to be irradiated with X-rays. Thereafter, an X-ray emitter which is located above the support plate irradiates the breast which is compressed by the compressor with X-rays, thereby finally acquiring an X-ray image which may be used for observing an inner structure of the breast.

SUMMARY

Therefore, it is an aspect of one or more exemplary embodiments to provide an X-ray imaging apparatus and an X-ray image processing method in which X-ray images which correspond to a greater number of various X-ray emission positions may be acquired by using X-ray images which are captured at a small number of X-ray emission positions.

It is another aspect of one or more exemplary embodiments to provide an X-ray imaging apparatus and an X-ray image processing method in which a plurality of stereoscopic X-ray images and/or a multi-view image with respect to various angles may be acquired by capturing X-ray images at a relatively small number of X-ray emission positions.

It is a further aspect of one or more exemplary embodiments to provide an X-ray imaging apparatus and an X-ray image processing method in which a continuous stereoscopic X-ray image may be displayed by using X-ray images which correspond to a relatively small number of X-ray emission positions.

Additional aspects of the exemplary embodiments will be set forth in part in the description which follows and, in part, will be obvious from the description, or may be learned by practice of the exemplary embodiments.

To achieve the above-described technical goals, there are provided an X-ray imaging apparatus and an X-ray image processing method.

In accordance with one aspect of one or more exemplary embodiments, an X-ray imaging apparatus includes at least one X-ray emitter which is configured to irradiate an object with X-rays at a plurality of X-ray emission positions, an X-ray detector which is configured to detect a plurality of X-rays which have been emitted by the at least one X-ray emitter and propagated through the object, and to convert the detected X-rays into an electric signal, and an image processor which is configured to acquire a plurality of original X-ray images which respectively correspond to the X-ray emission positions from the generated electric signal, and to estimate a virtual X-ray image which is acquirable at an additional X-ray emission position which is located between at least two of the plurality of X-ray emission positions, based on at least two of the plurality of original X-ray images.

The image processor may be further configured to generate a stereoscopic X-ray image which is based on two X-ray images from among the plurality of original X-ray images and the estimated virtual X-ray image, or to generate a multi-view image of the object which includes views which correspond to at least two angles, and to display the generated stereoscopic X-ray image and/or the generated multi-view image.

In accordance with another aspect of one or more exemplary embodiments, an X-ray imaging apparatus includes an X-ray emitter which is movable to each of a plurality of X-ray emission positions and which is configured to irradiate an object with X-rays at each of the X-ray emission positions, an X-ray detector which is movable to each of a plurality of light receiving positions and which is configured to detect X-rays at each of the light receiving positions, and to convert the detected X-rays into at least one electric signal, a movement controller which is configured to simultaneously or sequentially rotate the X-ray emitter and the X-ray detector about a rotating shaft which is disposed between the X-ray emitter and the X-ray detector such that the X-ray emitter faces the X-ray detector, and an image processor which is configured to generate a plurality of original X-ray images which respectively correspond to the X-ray emission positions from the generated at least one electric signal and estimate and generate a virtual X-ray image which is acquirable at an additional X-ray emission position which is located between at least two of the plurality of X-ray emission positions, based on at least two of the plurality of original X-ray images.

In accordance with another aspect of one or more exemplary embodiments, an X-ray image processing method includes irradiating, by an X-ray emitter which is included in an X-ray imaging apparatus, an object with X-rays at a plurality of X-ray emission positions, receiving, by an X-ray detector which is included in the X-ray imaging apparatus, the irradiated X-rays and converting the received X-rays into at least one electric signal, acquiring a plurality of original X-ray images which respectively correspond to the plurality of X-ray emission positions by reading out at least one X-ray image from the at least one electric signal, and estimating, based on at least two of the acquired plurality of original X-ray images, a virtual X-ray image which is acquirable at a virtual X-ray emission position which is located between the at least two X-ray emission positions which correspond to the at least two of the acquired plurality of original X-ray images.

In accordance with further aspect of one or more exemplary embodiments, an X-ray image processing method includes irradiating, by an X-ray imaging apparatus, an object with X-rays at a plurality of X-ray emission positions, receiving the irradiated X-rays and converting the received X-rays into at least one electric signal, acquiring a plurality of original X-ray images which respectively correspond to the X-ray emission positions by reading out at least one X-ray image from the at least one electric signal, converting at least one of the acquired plurality of original X-ray images in order to generate at least one full isocentric X-ray image, and estimating, based on at least two of the plurality of original X-ray images and the at least one full isocentric X-ray image, a virtual X-ray image which corresponds to a virtual X-ray emission position which is located between the at least two X-ray emission positions which correspond to the at least two of the acquired plurality of original X-ray images.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
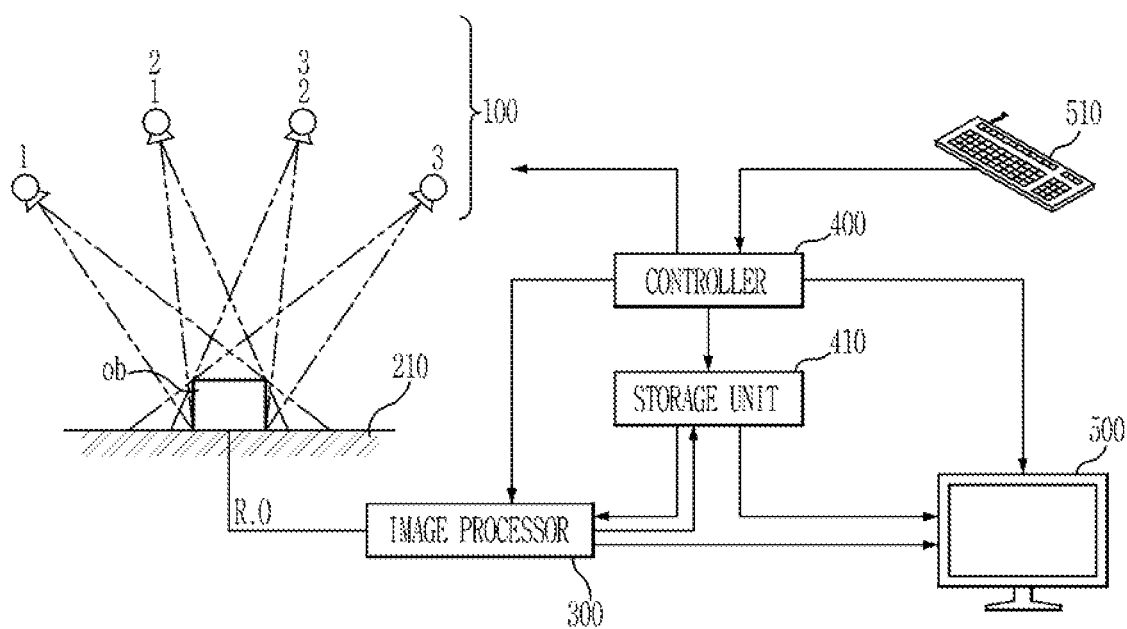
FIG. 1 is a general view of an X-ray imaging apparatus, according to an exemplary embodiment.

Reference will now be made in detail to exemplary embodiments, examples of which are illustrated in the accompanying drawings, wherein like reference numerals refer to like elements throughout.

Hereinafter, exemplary embodiments of an X-ray imaging apparatus will be described in detail with reference to FIGS. 1 through 6.

FIG. 1 is a general view of an X-ray imaging apparatus, according to an exemplary embodiment.

As illustrated in FIG. 1, the X-ray imaging apparatus may include an X-ray emitter 100 which is configured to generate X-rays and irradiate an object ob with the generated X-rays at a plurality of emission positions, an X-ray detector 210 which is configured to detect X-rays irradiated by the X-ray emitter 100 and to convert the detected X-rays into an electric signal, and an image processor 300 which is configured to read out and generate an X-ray image from the electric signal generated by the X-ray detector 210 and to generate a new X-ray image by performing predetermined image processing on the generated X-ray image or to generate a new X-ray image from the generated X-ray image by performing particular image processing processes.

The X-ray emitter 100 includes an X-ray tube which is configured to generate X-rays. The X-ray tube includes a filament of a cathode and an anode. When a predetermined voltage is applied between opposite terminals of the X-ray tube, electrons of the filament of the cathode of the X-ray tube are accelerated in correspondence with the applied voltage and move towards the anode. When the electrons collide with the anode and thus are decelerated, electromagnetic waves having strong material penetrating power, i.e., X-rays, are emitted according to the law of conservation of energy.

The emitted X-rays may be controlled by a collimator or the like to be radiated within a certain range in a predetermined direction, e.g., towards an object.

According to an exemplary embodiment, the X-ray imaging apparatus may include at least one X-ray emitter 100. In this regard, the at least one X-ray emitter 100 is movable to any one or more of a plurality of X-ray emission positions, and thus a plurality of X-ray images which respectively correspond to various angles of irradiation may be acquired by irradiating an object ob with X-rays a plurality of times after movement of the X-ray emitter 100 to each of the plurality of X-ray emission positions.

According to another exemplary embodiment, the X-ray imaging apparatus may include a plurality of X-ray emitters 100. The X-ray emitter 100 may acquire X-ray images which respectively correspond to a plurality of angles with respect to the object ob by simultaneously or non-simultaneously (e.g., sequentially) irradiating the object ob with X-rays at each of a plurality of X-ray emission positions.

To be distinguished from a virtual X-ray emission position at which a virtual X-ray image is obtainable, which will be described below, i.e., a virtual X-ray emission position, an actual X-ray emission position of the X-ray emitter 100 is referred to as an original X-ray emission position. In addition, an X-ray image which is acquired through X-rays radiated at the original X-ray emission position is referred to as an original X-ray image.

The X-ray imaging apparatus may further include a controller 400 which is configured to control an overall operation of the X-ray emitter 100, the X-ray detector 210, and the image processor 300. In particular, the controller 400 may be configured to generate a control command for movement of the at least one X-ray emitter 100 to any one or more of various emission positions or for X-ray emission timing control of the X-ray emitters 100 with respect to the object ob and to transmit the generated control command to the X-ray emitter(s) 100.

The X-ray imaging apparatus may further include a storage unit 410 which is configured to store an X-ray image generated by the image processor 300, an X-ray image which is obtained by image processing performed by the image processor 300, various information related thereto, and/or the like.

In addition, the X-ray imaging apparatus may further include a display unit 500, for example, a monitor, which is configured to display the X-ray image acquired by the image processor 300 and/or the X-ray image obtained by image processing performed by the image processor 300 to a user.

In an exemplary embodiment, the display unit 500 may include a touch-screen that includes a touch panel and receives a predetermined command based on a touch operation performed by a user.

According to an exemplary embodiment, the X-ray imaging apparatus may further include an input unit 510 via which predetermined commands and/or data are input, such as any one or more of a keyboard, a mouse, a tablet, and a tablet pen.

Hereinafter, X-ray emitters according to various exemplary embodiments will be described with reference to FIGS. 2 and 3.

Figure 2:
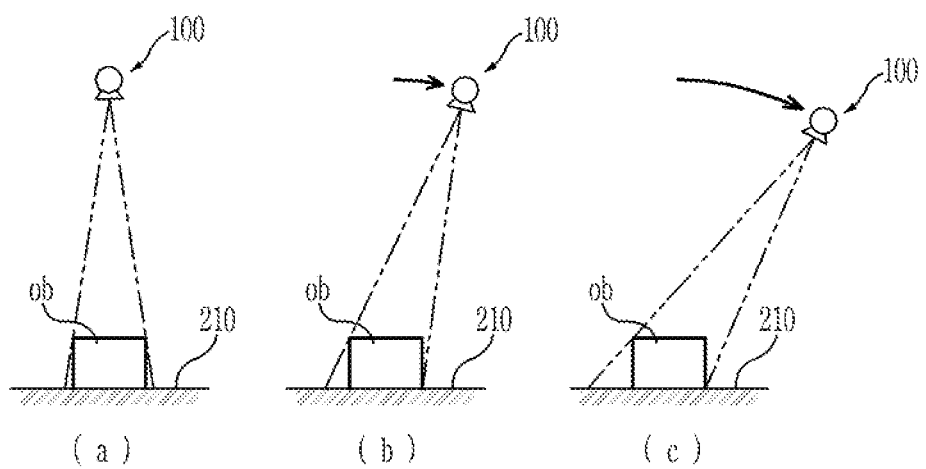
FIG. 2 is a conceptual view of an X-ray emitter, according to an exemplary embodiment.

FIG. 2 is a conceptual view of an X-ray emitter, according to an exemplary embodiment.

As illustrated in FIG. 2, the X-ray imaging apparatus may include a single X-ray emitter, which is designated by reference numeral 100. As illustrated in drawing (a) on the left-side portion of FIG. 2, the X-ray emitter 100 may irradiate an object ob with X-rays at a specific position that is vertically upward with respect to the object ob, i.e., the original X-ray emission position.

The X-ray emitter 100 may be moved to other positions, as illustrated in drawing (b) in the center portion of FIG. 2 and drawing (c) on the right-side portion of FIG. 2. In this case, the X-ray emitter 100 may be moved only in one direction or in both left and right directions. In addition, as illustrated in FIG. 2, the X-ray emitter 100 may be moved along a predetermined axis, e.g., a predetermined arc about the object ob.

The X-ray emitter 100 may be moved after irradiating the object ob with X-rays as illustrated in drawing (a) of FIG. 2, or may be first moved to other positions, i.e., the original X-ray emission position, before irradiation of the object with X-rays, if necessary or desirable.

The X-ray emitter 100 may irradiate the object ob with X-rays at another original X-ray emission position after being moved.

In particular, the X-ray emitter 100 may be moved to each of a plurality of predetermined positions and thus irradiate the object ob with X-rays at each of a plurality of different original X-ray emission positions, and the X-ray detector 210 may receive the X-rays which are emitted by the X-ray emitter 100 at each of the original X-ray emission positions and convert the received X-rays which respectively correspond to each of the original X-ray emission positions into a respective electric signal, whereby the X-ray imaging apparatus may acquire original X-ray images obtained by X-ray imaging at each of various different angles.

Figure 3:
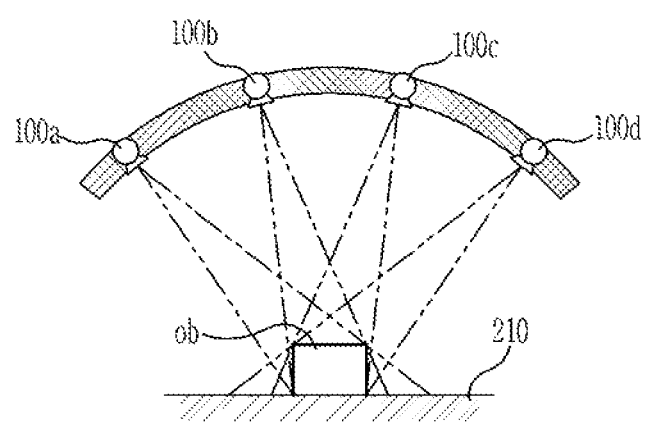
FIG. 3 is a conceptual view of an X-ray emitter, according to another exemplary embodiment.

FIG. 3 is a conceptual view of an X-ray emitter, according to another exemplary embodiment.

The X-ray imaging apparatus may include a plurality of X-ray emitters 100a, 100b, 100c, and 100d as illustrated in FIG. 3.

Each of the X-ray emitters 100a, 100b, 100c, and 100d may irradiate an object ob with X-rays at respective installation positions, i.e., a plurality of original X-ray emission positions, and the X-ray detector 210 detects the X-rays emitted by each of the X-ray emitters 100a, 100b, 100c, and 100d, thereby acquiring original X-ray images obtained by X-ray imaging at each of the original X-ray emission positions, i.e., at each of various different angles.

In this case, the X-ray emitters 100a, 100b, 100c, and 100d may simultaneously irradiate the object ob with X-rays. When the X-ray emitters 100a, 100b, 100c, and 100d simultaneously irradiate the object ob with X-rays, the X-ray imaging apparatus may include a plurality of X-ray detectors 210 which respectively correspond to the X-ray emitters 100a, 100b, 100c, and 100d.

Alternatively, the X-ray emitters 100a, 100b, 100c, and 100d may non-simultaneously irradiate the object ob with X-rays. In this case, the X-ray emitters 100a, 100b, 100c, and 100d may sequentially irradiate the object with X-rays in a predetermined order, and the X-ray detector 210 may detect the X-rays which have been sequentially emitted and then convert the detected X-rays into at least one electric signal.

The X-ray emitters 100a, 100b, 100c, and 100d may also be moved to other positions, as described above with reference to FIG. 2. Thus, the X-ray emitters 100a, 100b, 100c, and 100d may emit X-rays at a greater number of original X-ray emission positions than the number of the X-ray emitters 100a, 100b, 100c, and 100d (i.e., for example, four) and, accordingly, a plurality of original X-ray images at various angles which respectively correspond to the original X-ray emission positions may be acquired.

Hereinafter, X-ray detectors according to various exemplary embodiments will be described with reference to FIGS. 4 and 5.

Figure 4:
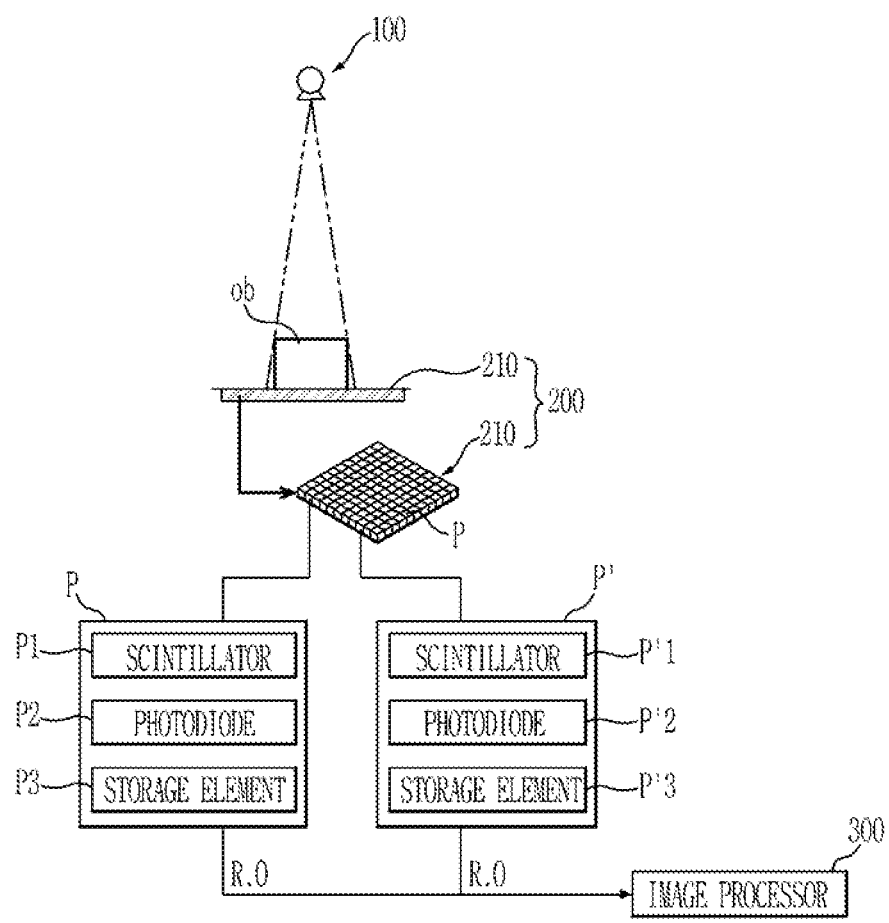
FIG. 4 is a conceptual view of an X-ray detector, according to an exemplary embodiment.

FIG. 4 is a conceptual view of an X-ray detector 200, according to an exemplary embodiment.

As illustrated in FIG. 4, according to an exemplary embodiment, the X-ray imaging apparatus may include the X-ray detector 200 which is configure to detect X-rays emitted from the X-ray emitter 100 and to convert the detected X-rays into an electric signal, and the X-ray detector 200 may include an X-ray detection panel 210 which is configured to receive X-rays.

The X-ray detection panel 210 includes a plurality of pixels P and P', and the pixels P and P' may respectively include scintillators P1 and P'1 which are configured to output visible photons upon receiving X-rays, photodiodes P2 and P'2 which are configured to sense the photons output from the scintillators P1 and P'1 and to output electric signals which correspond to the sensed photons, and storage elements P3 and P'3 (e.g., a storage capacitor) which are configured to store the electric signals output from the photodiodes P2 and P'2.

The electric signals stored by the storage elements P3 and P'3 are read out by the image processor 300, and the image processor 300 generates an X-ray image by performing a combination of electric signals of the respective pixels P and P'.

As illustrated in FIG. 4, the X-ray imaging apparatus according to an exemplary embodiment may include a single fixed X-ray detection panel 210, and the X-ray detection panel 210 detects X-rays which are emitted at a plurality of different original X-ray emission positions as illustrated in FIGS. 2 and 3 and then stores the detected X-rays as an electric signal.

Figure 5:
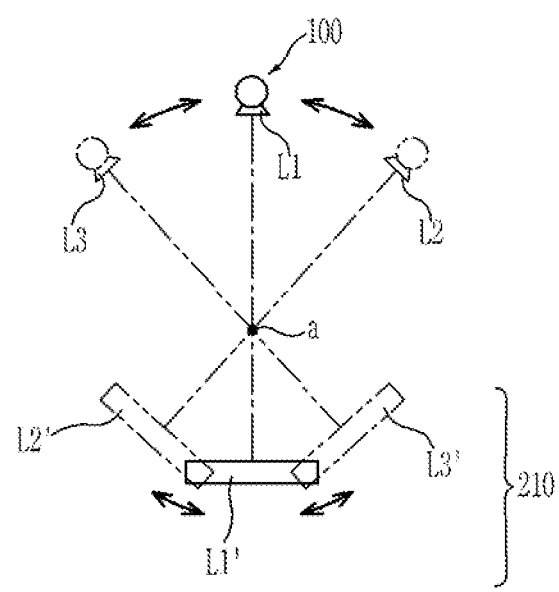
FIG. 5 is a conceptual view of an X-ray detector, according to another exemplary embodiment.

Different from the above-illustrated exemplary embodiment, in an X-ray imaging apparatus according to another exemplary embodiment, as illustrated in FIG. 5, an X-ray detection panel 210 of an X-ray detector 200 may receive X-rays which are emitted from an X-ray emitter 100 after being moved or while being moved.

FIG. 5 is a conceptual view of the X-ray detector 200, according to another exemplary embodiment.

As illustrated in FIG. 5, the X-ray detector 200, in particular, the X-ray detection panel 210, may be moved in accordance with a movement of the X-ray emitter 100 to be symmetrical to the X-ray emitter 100 based on a predetermined central point a, and then detect X-rays which are emitted from the X-ray emitter 100.

FIGS. 1 and 2 illustrate a case in which the X-ray emitter 100 irradiates the object with X-rays at a plurality of original X-ray emission positions, and the X-ray detection panel 210 which is configured to detect the emitted X-rays remains in a fixed state. In the fixed state of the X-ray detection panel 210, when the X-ray emitter 100 is disposed vertically upward from the object ob as illustrated in drawing (a) of FIG. 2, there is relatively little distortion in the captured image for the object ob. Conversely, when the X-ray emitter 100 performs X-ray emission at a lateral upward position, i.e., at an oblique angle, the captured image may include severe distortion due to perspective effects. In particular, the severity of distortion increases as a measure of the oblique angle increases.

In the X-ray imaging apparatus according to the exemplary embodiment illustrated in FIG. 5, in order to address the distortion of the X-ray image, the X-ray detection panel 210 may be moved in correspondence with a movement of the X-ray emitter 100. In particular, when the X-ray emitter 100 is positioned at a first location L1, the X-ray detection panel 210 may be positioned at a corresponding first location L1' that is opposite to the first location L1 based on the predetermined central point a. In addition, when the X-ray emitter 100 is moved to a second or third position L2 or L3, the X-ray detection panel 210 may also be moved to a corresponding second or third location L2' or L3' in order to face the X-ray emitter 100 based on the predetermined central point a.

In an X-ray imaging apparatus according to another exemplary embodiment, to address the distortion of the X-ray image, a capture image is converted to correct the distortion of the X-ray image, thereby generating a full isocentric image. This will be described below.

Figure 6:
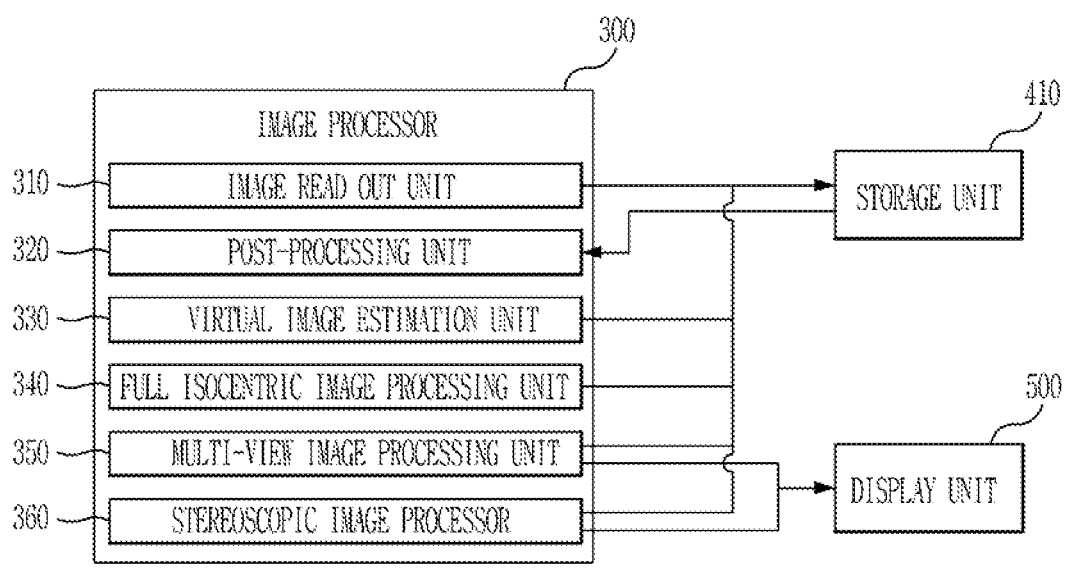
FIG. 6 is a block diagram which illustrates an image processor, according to an exemplary embodiment.

Hereinafter, the image processor 300 will be described with reference to FIG. 6. FIG. 6 is a block diagram which illustrates the image processor 300, according to an exemplary embodiment. As illustrated in FIG. 6, in the X-ray imaging apparatus according to the exemplary embodiment, the image processor 300 may include an image read out unit 310 which is configured to read out and generate an original X-ray image from an electric signal which corresponds to the detected X-rays and, if necessary, to enable the storage unit 410 to store the original X-ray image, a post-processing unit 320 which is configured to perform predetermined post-processing on the original X-ray image generated by the image read out unit 310 or retrieved from the storage unit 410, and a virtual image estimation unit 330 which is configured to estimate a virtual X-ray image.

In the X-ray imaging apparatus according to the exemplary embodiment, the virtual image estimation unit 330 may acquire a virtual X-ray image based on at least two original X-ray images obtained by the image read out unit 310. In addition, according to another exemplary embodiment, the virtual image estimation unit 330 may acquire another virtual X-ray image based on at least two virtual X-ray images generated by the virtual image estimation unit 300. Moreover, according to another exemplary embodiment, the virtual image estimation unit 330 may estimate another virtual X-ray image based on the original X-ray images and the virtual X-ray image. In particular, the virtual image estimation unit 330 acquires a virtual X-ray image based on the original X-ray images by performing a calculation.

The virtual X-ray image estimated by the virtual image estimation unit 330 includes an X-ray image which is generated by virtually performing X-ray emission at a virtual X-ray emission position which is different from the original X-ray emission position. In this case, the virtual X-ray emission position may be disposed between at least two original X-ray emission positions at which the X-ray emitter 100 performs X-ray emission in order to acquire at least two original X-ray images which may then be used to estimate the virtual X-ray image.

As described above, the virtual X-ray emission position may be disposed between the at least two original X-ray emission positions. In addition, the virtual X-ray emission position may be disposed between at least two virtual X-ray emission positions, or between an original X-ray emission position and a virtual X-ray emission position.

According to an exemplary embodiment, a virtual X-ray image may be generated by applying a respective weight to a corresponding original X-ray image based on a distance between a virtual X-ray emission position which corresponds to the virtual X-ray image and two original X-ray emission positions.

In particular, in order to generate the virtual X-ray image, the virtual X-ray image may be estimated by calculating the virtual X-ray image by applying a greater weight to an original X-ray image at one of the two original X-ray emission positions which is relatively close to the virtual X-ray emission position corresponding to the virtual X-ray image and applying a smaller weight to the other of the two original X-ray emission positions which is relatively far from the virtual X-ray emission position, and then performing a calculation based on the applied weights.

In this case, as described above, only the original X-ray image may not be used but the virtual X-ray image may also be used for estimation of the virtual X-ray image. In particular, a virtual X-ray image may be estimated and generated by performing a calculation such that a greater weight is applied to an image which is relatively close to the virtual X-ray emission position corresponding to the virtual X-ray image, wherein the image to which the greater weight is applied may be one of two virtual X-ray images which correspond to the two virtual X-ray emission positions or one of the original X-ray images at the corresponding original X-ray emission position and the virtual X-ray image at the virtual X-ray emission position, and a smaller weight is applied to an original X-ray image at the other of the two original X-ray emission positions which is relatively far from the virtual X-ray emission position or the virtual X-ray image at the virtual X-ray emission position.

In addition, the virtual image estimation unit 330 may use a motion prediction method in order to estimate the virtual X-ray image. This operation will be described below.

In the X-ray imaging apparatus according to the exemplary embodiment, the image processor 300 may further include a full isocentric image processing unit 340.

The full isocentric image processing unit 340 is configured to convert at least one of the original X-ray images in order to generate at least one full isocentric X-ray image. As described above, when the X-ray emitter 100 performs X-ray emission in a lateral direction in a fixed state of the X-ray detection panel 210, distortion occurs in the X-ray image due to X-ray emission in a lateral direction. The full isocentric image processing unit 340 may correct the distortion of the X-ray image by performing predetermined image processing processes in order to generate a full isocentric X-ray image that is the same as or similar to an X-ray image captured in such a manner that the X-ray detection panel 210 receives X-rays while in motion.

In the X-ray imaging apparatus according to the exemplary embodiment, the image processor 300 may further include a multi-view image processing unit 350.

The multi-view image processing unit 350 is configured to generate multi-view images that display an object from multiple views by matching two X-ray images which are captured at adjacent X-ray emission positions from among original X-ray images and virtual X-ray images by using a method such as extraction of feature points, or the like.

In addition, in the X-ray imaging apparatus according to the exemplary embodiment, the multi-view image processing unit 350 may match two stereoscopic images which are captured at adjacent original X-ray emission positions or virtual X-ray emission positions from among stereoscopic images which are generated from original X-ray images and/or virtual X-ray images, in order to generate multi-view images based on the stereoscopic images. The generation of the stereoscopic images from the original X-ray images and/or the virtual X-ray images may be performed by a stereoscopic image processor 360.

The imaging processor 300 of the X-ray imaging apparatus according to the exemplary embodiment may further include the stereoscopic image processor 360.

The stereoscopic image processor 360 may generate a stereoscopic image by using an original X-ray image, a virtual X-ray image, or the original X-ray image and the virtual X-ray image, or may perform image processing or control output of the captured X-ray image so as for the stereoscopic image to be displayed on the display unit 500.

A stereoscopic image is an image that enables a viewer to acquire 3D effects from images or video which is regenerated by using binocular parallax caused by a distance between pupils of human eyes. The eyes of a human are approximately 6 cm apart, which causes a slight difference between an image seen by the left eye and an image seen by the right eye. Through such slight difference, a human brain may recognize 3D-effects.

Thus, when the stereoscopic image is displayed, a left-eye image perceived by the left eye and a right-eye image perceived by the right eye may be output so that a human body may view an image which is displayed on the display unit 500 in a stereoscopic manner.

In this case, there are various stereoscopic image reconstruction methods which are based on an output method of a left-eye image and a right-eye image or a method of perceiving the left-eye image and the right-eye image by the left and right eyes of a user.

A user may view the stereoscopic image by using a glasses method in which the user wears glasses, or a non-glasses method. Examples of the glasses method include a red-and-blue glasses method, a polarized glasses method (a space division method), and a shutter glasses method (a time-split method), and examples of the non-glasses method include a lenticular sheet method and a barrier plate method.

According to an exemplary embodiment, for example, when the red-and-blue glasses method is used, the stereoscopic image processor 360 may display or generate a stereoscopic image by overlapping a left-eye image and a right-eye image in order to display the overlapping images on a screen, or the stereoscopic image processor 360 may generate a new image that may be displayed in such manner.

According to another exemplary embodiment, for example, when the polarized glasses method is used, the stereoscopic image processor 360 may generate a stereoscopic image or display a stereoscopic image on a screen by splitting a left-eye image and a right-eye image and combining the split left-eye and right-eye images.

According to another exemplary embodiment, for example, when the shutter glasses method is used, the stereoscopic image processor 360 controls the display unit 500 to sequentially display a left-eye image and a right-eye image in an alternating manner so that that alternatingly displayed left-eye and right-eye images may be perceived by the right and left eyes.

Hereinafter, X-ray imaging methods according to various exemplary embodiments will be described in detail with reference to FIGS. 7 through 23.

Figure 7:
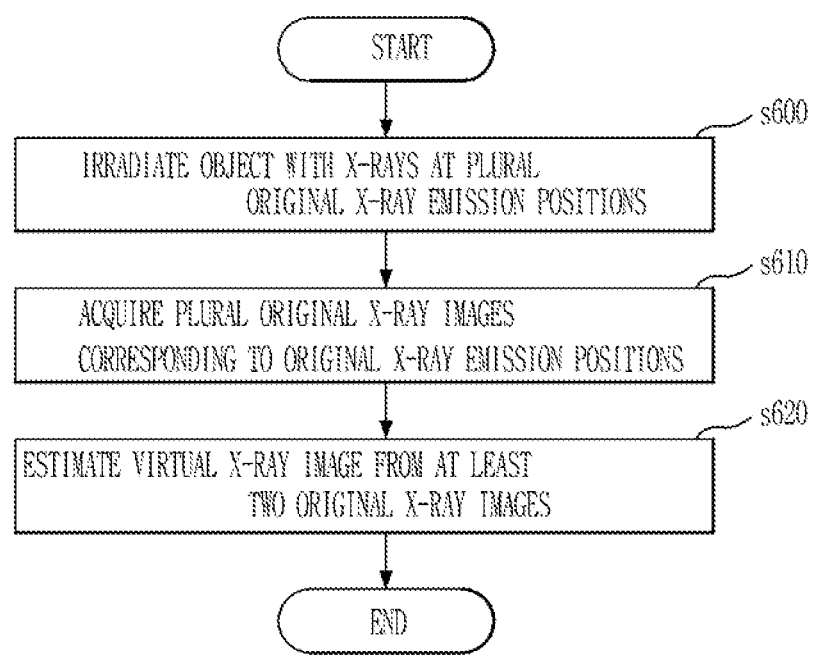
FIG. 7 is a flowchart which illustrates an X-ray image processing method, according to an exemplary embodiment.

FIG. 7 is a flowchart which illustrates an X-ray imaging method, according to an exemplary embodiment.

The X-ray imaging method according to an exemplary embodiment, as illustrated in FIG. 7, includes irradiating an object ob with X-rays at a plurality of original X-ray emission positions in operation s600, acquiring a plurality of original X-ray images corresponding to the original X-ray emission positions in operation s610, and estimating a virtual X-ray image by using at least two original X-ray images from among the plurality of original X-ray images in operation s620.

First, the irradiation of the object ob with X-rays at a plurality of original X-ray emission positions in operation s600 and the acquisition of the plurality of original X-ray images corresponding to the original X-ray emission positions in operation s610 will be described with reference to FIG. 8.

Figure 8:
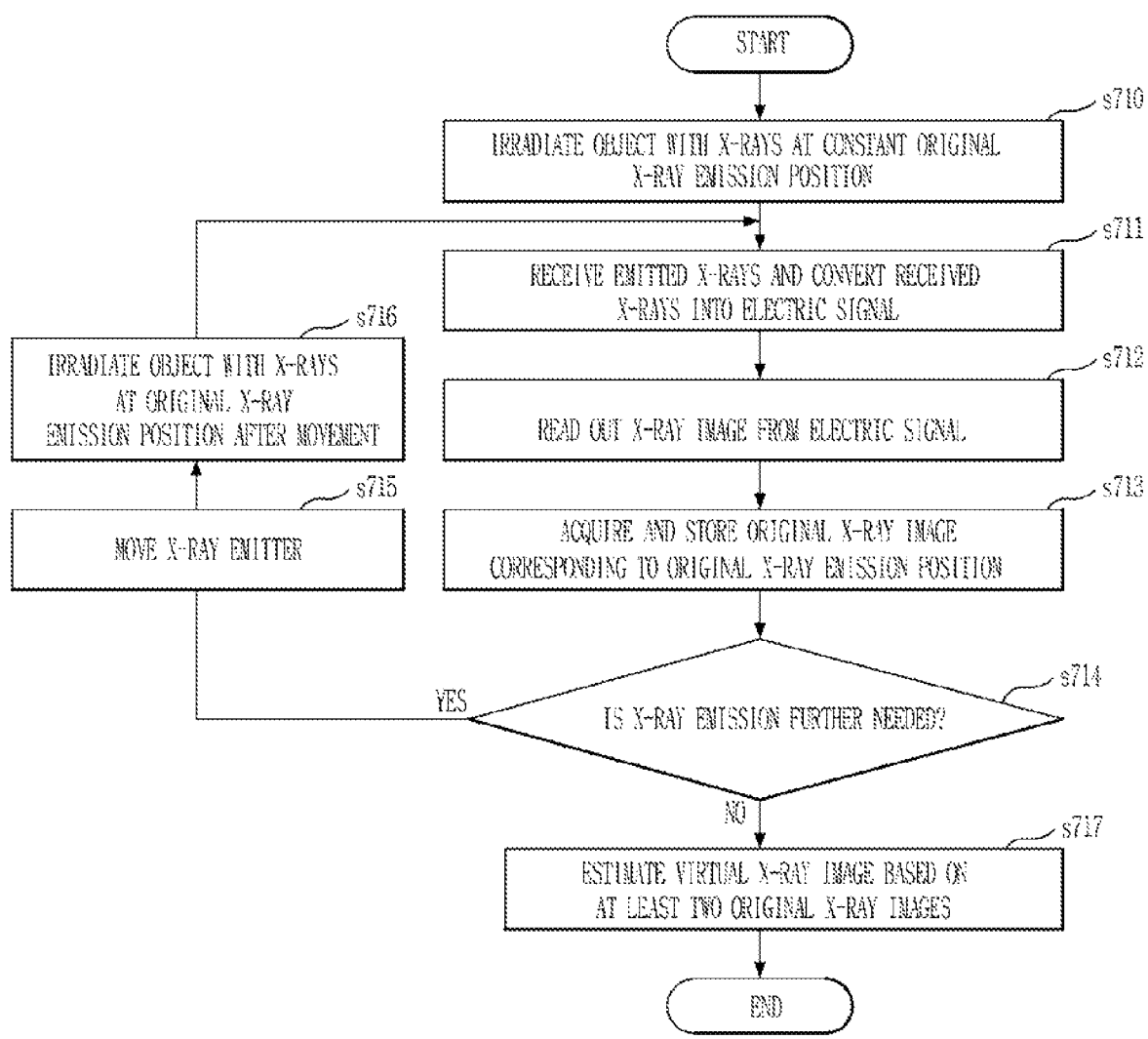
FIG. 8 is a flowchart which illustrates a process for acquiring X-ray images, according to an exemplary embodiment.

FIG. 8 is a flowchart which illustrates a process for acquiring original X-ray images, according to an exemplary embodiment.

According to an exemplary embodiment, as illustrated in FIG. 8, in order to acquire an original X-ray image, first, in operation s710, at least one X-ray emitter 100 which is movable to any of a plurality of original X-ray emission positions irradiates an object ob with X-rays at a predetermined original X-ray emission position. The X-rays emitted from the X-ray emitter 100 propagate through the object ob or are directly received by the X-ray detection panel 201 of the X-ray detector 200 without propagating through the object ob. Then, in operation s711, each of a plurality of pixels P of the X-ray detection panel 210 receives the emitted X-rays by using the scintillator P1 and the photodiode P2, converts the received X-rays into an electric signal, and stores the electric signal in the storage element P3.

In operation s712, the image processor 300 reads out an original X-ray image which corresponds to the predetermined original X-ray emission position by reading the electric signal from the storage element P3 of each pixel P.

As a result, in operation s713, the original X-ray image which corresponds to the predetermined original X-ray emission position is acquired, and the acquired original X-ray image is stored in the storage unit 410 under control of the controller 400. In this regard, metadata which relates to the original X-ray emission position corresponding to the original X-ray image is stored together with the original X-ray image under control of the controller 400, and thus, the acquired original X-ray image may be distinguished from an original X-ray image which is acquired through X-ray emission at another original X-ray emission position.

When a greater number of original X-ray images further needs to be acquired as determined in operation s714, the X-ray emitter 100 is moved to other original X-ray emission positions based on user control or control of the controller 400 as indicated by a pre-stored setting in operation s715.

After movement of the X-ray emitter 100, in operation s716, the object ob is irradiated with X-rays at another original X-ray emission position.

Then, as illustrated in FIG. 8, an X-ray image which corresponds another original X-ray emission position is acquired by repeating operations s711, s712, and s713, and a plurality of original X-ray images which respectively correspond to various original X-ray emission positions may be acquired by repeating operations s711 through s716.

Thereafter, when a determination is made in operation s714 that there is no need for additional original X-ray images, the image processor 300 estimates a virtual X-ray image based on at least two original X-ray images from among the original X-ray images which correspond to the various original X-ray emission positions in operation s717.

According to another exemplary embodiment, the X-ray imaging apparatus may include the X-ray emitters 100a, 100b, 100c, and 100d, as illustrated in FIG. 3.

In this case, as illustrated in FIG. 8, first, any one of the X-ray emitters 100a. 100b, 100c, and 100d, e.g., the X-ray emitter 100a, irradiates an object ob with X-rays in a fixed state, and the X-ray imaging apparatus acquires an X-ray image corresponding to the X-ray emitter 100a using the X-ray detector 200 and the image processor 300 and stores the acquired X-ray image. Thereafter, when a greater number of original X-ray images further needs to be acquired, as determined in operation s714, another X-ray emitter, e.g., the X-ray emitter 100b, irradiates the object ob with X-rays and the X-ray detector 200 detects the X-rays, thereby acquiring an X-ray image corresponding to the X-ray emitter 100b.

By repeating this process a plurality of times, a plurality of original X-ray images which respectively correspond to X-ray emission at each of a plurality of original X-ray emission positions may be acquired.

When the original X-ray images are acquired, a virtual X-ray image may be generated by using at least two original X-ray images from among the original X-ray images.

Hereinafter, a method for acquiring a virtual X-ray image by selecting at least two original X-ray images from among a plurality of original X-ray images and using the at least two original X-ray images, according to an exemplary embodiment, will be described.

Figure 9:
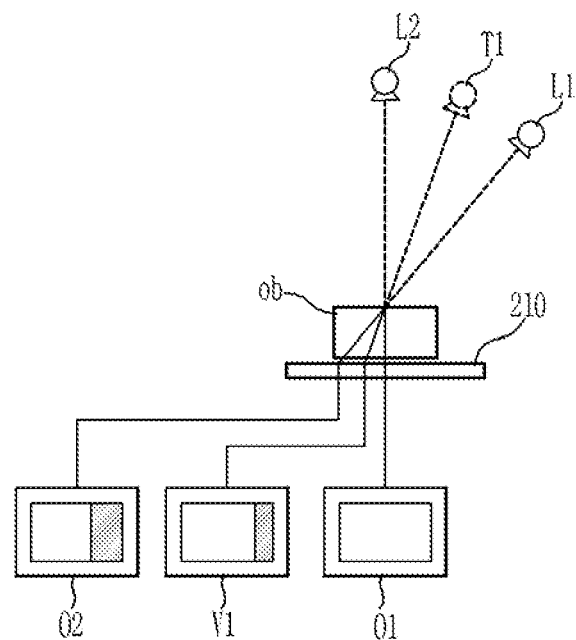
FIG. 9 is a view which illustrates a process for generating a virtual X-ray image by using original X-ray images, according to an exemplary embodiment.

FIG. 9 is a view which illustrates a process for generating a virtual X-ray image by using original X-ray images, according to an exemplary embodiment.

As illustrated in FIG. 9, a virtual X-ray image V1 is an X-ray image which is generated by performing X-ray imaging with respect to a virtual emission position at which the X-ray emitter 100 does not actually perform X-ray emission, i.e., a virtual X-ray emission position T1.

The virtual X-ray image V1 may be generated based on original X-ray images O1 and O2 which respectively correspond to original X-ray emission locations L1 and L2 at which the X-ray emitter 100 actually irradiates an object ob with X-rays.

In particular, based on the original X-ray images O1 and O2 of the object ob which are captured at the original X-ray emission locations L1 and L2, the virtual X-ray image V1 which is generated by virtual X-ray emission at the virtual X-ray emission position T1 which is disposed between the original X-ray emission locations L1 and L2 is generated without further X-ray imaging.

Figure 10:
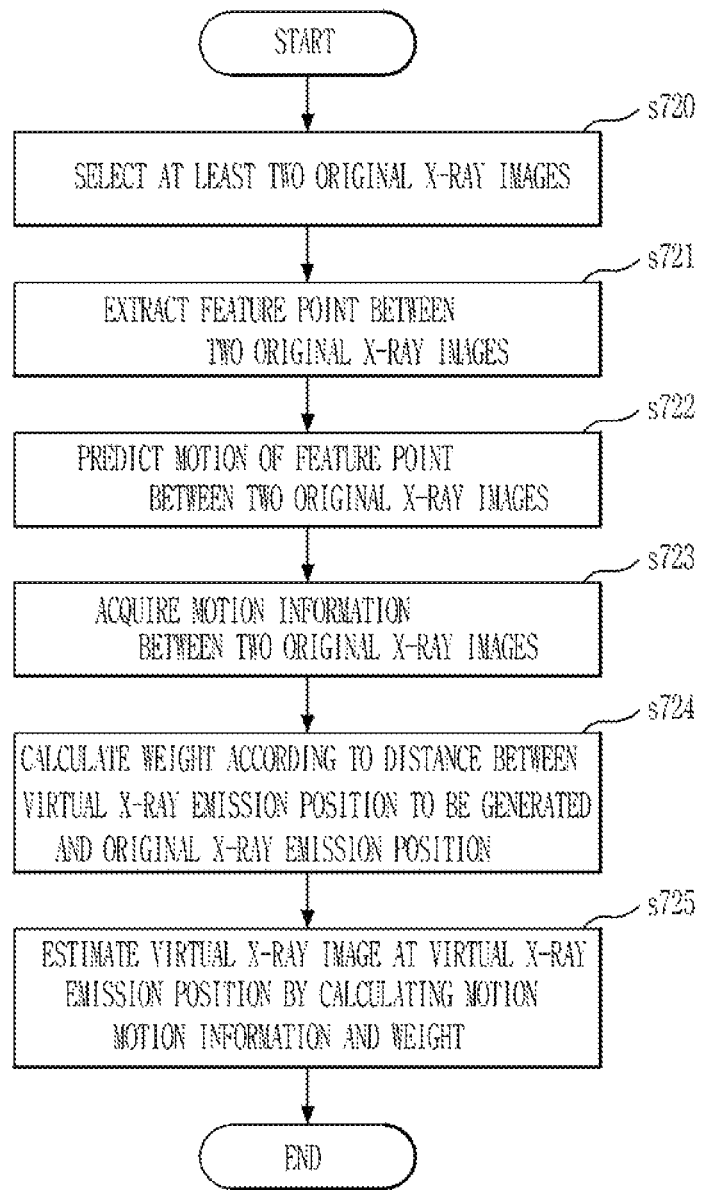
FIG. 10 is a flowchart which illustrates a process for generating a virtual X-ray image by using original X-ray images, according to an exemplary embodiment.

The method generating a virtual X-ray image is illustrated in FIG. 10.

Figure 11A:
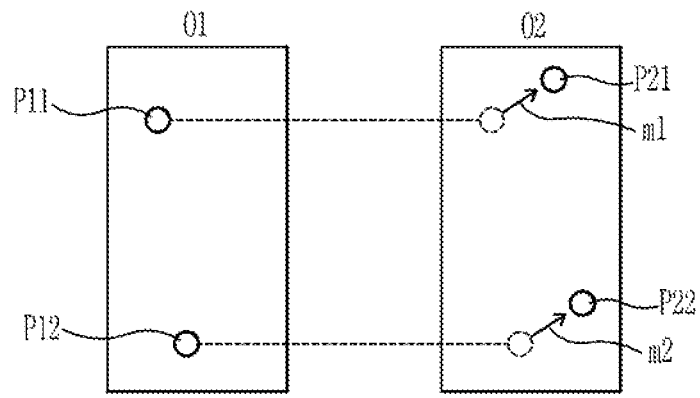
FIGS. 11A and 11B are views which illustrate a process for generating a virtual X-ray image by using original X-ray images, according to an exemplary embodiment.
Figure 11B:
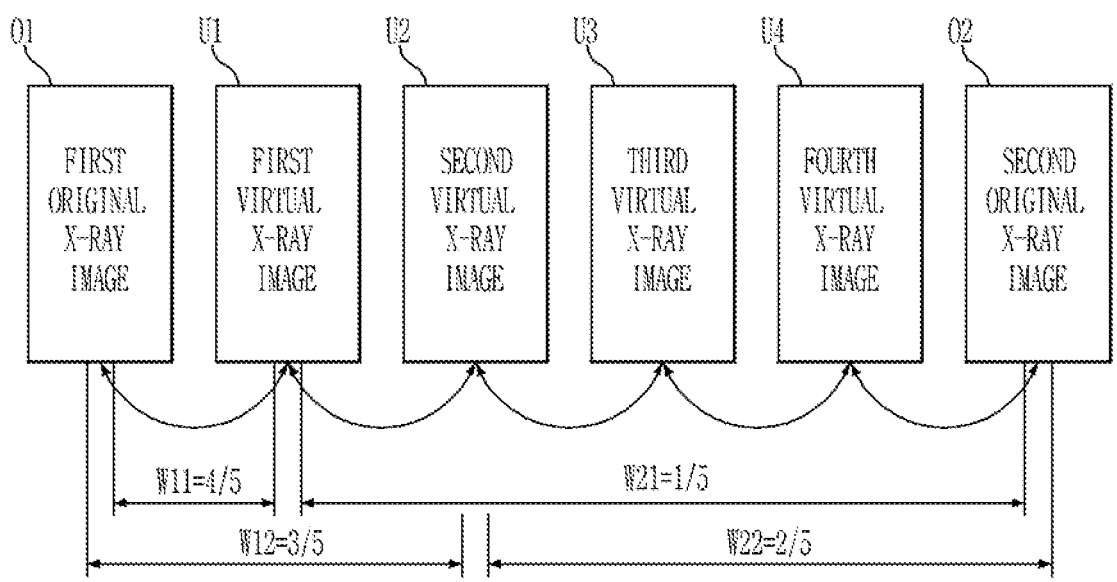
Figure 12:
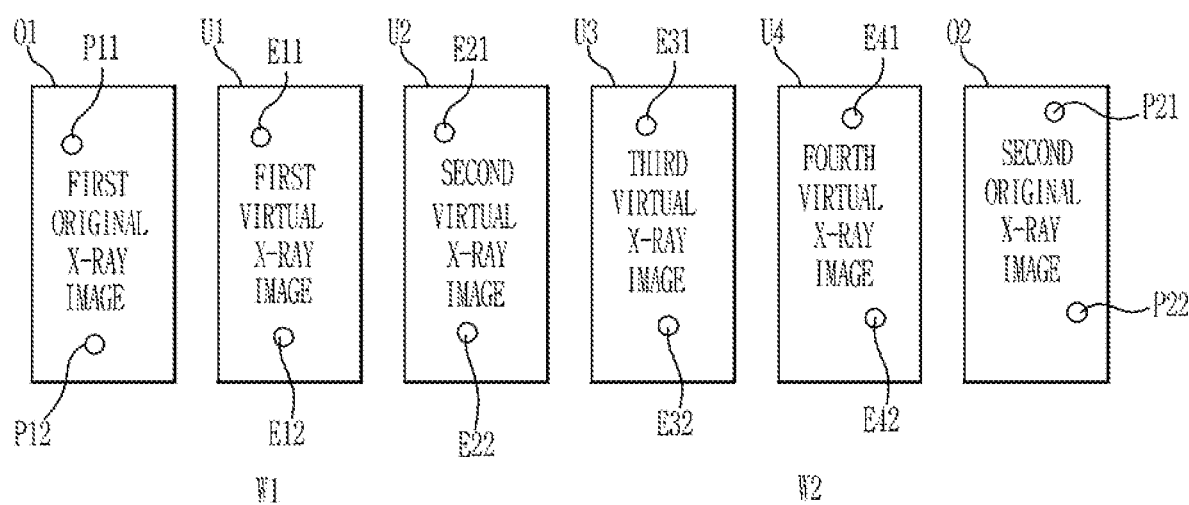
FIG. 12 is a view which illustrates a process for generating a virtual X-ray image by using original X-ray images, according to an exemplary embodiment.

FIG. 10 is a flowchart which illustrates a process of generating a virtual X-ray image by using original X-ray images, according to an exemplary embodiment. FIGS. 11A and 11B are views which illustrate a process for generating a virtual X-ray image by using original X-ray images, according to an exemplary embodiment. FIG. 12 is a view which illustrates a process for generating a virtual X-ray image by using original X-ray images, according to an exemplary embodiment.

According to an exemplary embodiment, as illustrated in FIG. 10, first, in operation s720, at least two of the original X-ray images which are acquired by using the above-described method are selected by the image processor 300 or the like.

According to an exemplary embodiment, in this case, the image processor 300 may select two X-ray images which are captured at adjacent original X-ray emission locations, i.e., a first original X-ray image O1 and a second original X-ray image O2.

Subsequently, in operation s721, as illustrated in FIGS. 10 and 11A, feature points P11 and P12 and feature points P21 and P22 (e.g., lesions or the like inside human tissues) of the respective original X-ray images O1 and O2 which respectively correspond to each other, may be used for comparison between the original X-ray images O1 and O2, and are distinguishable from other X-ray imaged tissues or structures inside the object ob, are extracted from the respective original X-ray images O1 and O2.

For example, as illustrated in FIG. 11A, the feature points P11 and P12 may be extracted from the first original X-ray image O1 which is captured at a first predetermined original X-ray emission position, and the feature points P21 and P22 that correspond to the feature points P11 and P12 of the first original X-ray image O1 may be extracted from the second original X-ray image O2 which is captured at another original X-ray emission position that is different from the first predetermined original X-ray emission position.

In this regard, because the first and second original X-ray images O1 and O2 are captured by X-ray emission at different X-ray emission positions, the feature points in the first and second original X-ray images O1 and O2, e.g., lesions, are present at different positions, although the same lesions are X-ray photographed.

In particular, in a comparison between the first and second original X-ray images O1 and O2, the feature points therein appear to move in a certain pattern as illustrated in FIG. 11A. In this aspect, the respective feature points in the first and second original X-ray images O1 and O2 seem to have a certain motion. As an example, as illustrated in FIG. 11A, the feature points P11 and P12 appear to move to respective locations which are indicated by the feature points P21 and P22, along certain respective movement paths m1 and m2.

Thus, motions of the first and second original X-ray images O1 and O2 may be predicted in operation s722 by using a motion prediction method for the above-described motion based on motions of the feature points P11, P12, P21, and P22 in the first and second original X-ray images O1 and O2, e.g., the movement motions m1 and m2 as illustrated in FIG. 11A. Based on prediction results, in operation s723, location values (coordinate values) for motion information on the first and second original X-ray images O1 and O2, e.g., points of each of the first and second original X-ray images O1 and O2 or vector values for movement of various tissues in the first and second original X-ray images O1 and O2, are obtained.

According to an exemplary embodiment, a plurality of virtual X-ray images which correspond to locations between the first and second original X-ray images O1 and O2 may be generated by using the obtained motion information.

According to an exemplary embodiment, as illustrated in FIG. 11B, in operation s724, in order to generate the virtual X-ray images which correspond to locations between the first and second original X-ray images O1 and O2 by using the obtained motion information, predetermined weights may be calculated based on the corresponding locations for the virtual X-ray images to be generated.

By applying the calculated weights to the first and second original X-ray images O1 and O2, a plurality of virtual X-ray images U1, U2, U3, and U4 may be generated in operation s725.

According to an exemplary embodiment, the virtual X-ray images U1, U2, U3, and U4 may be generated by applying predetermined weights to motion information obtained based on the virtual X-ray images U1, U2, U3, and U4 to be generated, e.g., location values (coordinate values) for points of each of the first and second original X-ray images O1 and O2, or vector values for movement of various tissues in the first and second original X-ray images O1 and O2, such as feature points.

According to an exemplary embodiment, as illustrated in FIG. 11B, the predetermined weights may be obtained based on respective distances between the virtual X-ray emission positions and the original X-ray emission positions.

In particular, in order to generate a virtual X-ray image (e.g., U1), a greater weight may be applied to one (e.g., the first original X-ray image O1 when the virtual X-ray image U1 is generated) of the two original X-ray images captured at one of the two original X-ray emission positions which is relatively close to the virtual X-ray emission position corresponding to the virtual X-ray image U1, and a smaller weight may be applied to the other (e.g., the original X-ray image O2) of the two original X-ray images captured at the other thereof which is relatively far from the virtual X-ray emission position corresponding to the virtual X-ray image U1.

In particular, as illustrated in FIG. 11B, when a first virtual X-ray image U1 is generated by using the first and second original X-ray images O1 and O2, a first weight W11, e.g., 4/5, may be applied to the first original X-ray image O1, and a second weight W21, e.g., 1/5, may be applied to the second original X-ray image O2, thereby generating the first virtual X-ray image U1.

Similarly, a second virtual X-ray image U2 may be generated by applying a third weight W12, e.g., 3/5, to the first original X-ray image O1 and applying a fourth weight W22, e.g., 2/5, to the second original X-ray image O2.

The number of the predetermined weights may be determined by using the number of virtual X-ray images to be generated between original X-ray images, i.e., the number of virtual X-ray emission positions between original X-ray emission positions.

By applying the predetermined weights as described above, a plurality of virtual X-ray images between the first and second original X-ray images O1 and O2, e.g., the first, second, third and fourth virtual X-ray images U1, U2, U3 and U4, may be finally generated as illustrated in FIG. 12.

Referring to FIG. 12, it may be confirmed that feature points E11, E12, E21, E22, E31, E32, E41 and E42 that respectively correspond to the feature points P11, P12, P21 and P22 of the first and second original X-ray images O1 and O2, e.g., lesions, are displayed in the generated first, second, third and fourth virtual X-ray images U1, U2, U3 and U4 similarly as in the first and second original X-ray images O1 and O2. The positions of feature points E11, E12, E21, E22, E31, E32, E41 and E42 of the respective first, second, third and fourth virtual X-ray images U1, U2, U3 and U4 are estimated based on motion information for motions m1 and m2 of the feature points P11, P12, P21 and P22 of the first and second original X-ray images O1 and O2, e.g., lesions, as described above.

As described above, virtual X-ray images (e.g., U1 and the like) which correspond to virtual X-ray emission positions (e.g., V1 and the like) disposed between two original X-ray emission positions L1 and L2 which correspond to the first and second original X-ray images O1 and O2 may be acquired based on the first and second original X-ray images O1 and O2. Thus, virtual X-ray images (e.g., U1) captured as if X-ray emission had been performed at the virtual X-ray emission position V1 may be acquired without performing X-ray imaging via separate X-ray emission at the virtual X-ray emission position V1.

In addition, according to an exemplary embodiment, a new virtual X-ray image may be further estimated based on the predicted virtual X-ray images (U1 and the like).

In particular, at least two virtual X-ray images may be selected from the virtual X-ray images (e.g., U1, U2, U3, and U4) instead of the original X-ray images (e.g., O1 and O2), and then another virtual X-ray image may be acquired by estimation based on the selected two virtual X-ray images.

In this regard, the selected two virtual X-ray images may include virtual X-ray images which are generated with respect to adjacent virtual X-ray emission positions.

Hereinafter, a process for generating a full isocentric image will be described with reference to FIGS. 13, 14, and 15.

Figure 13:
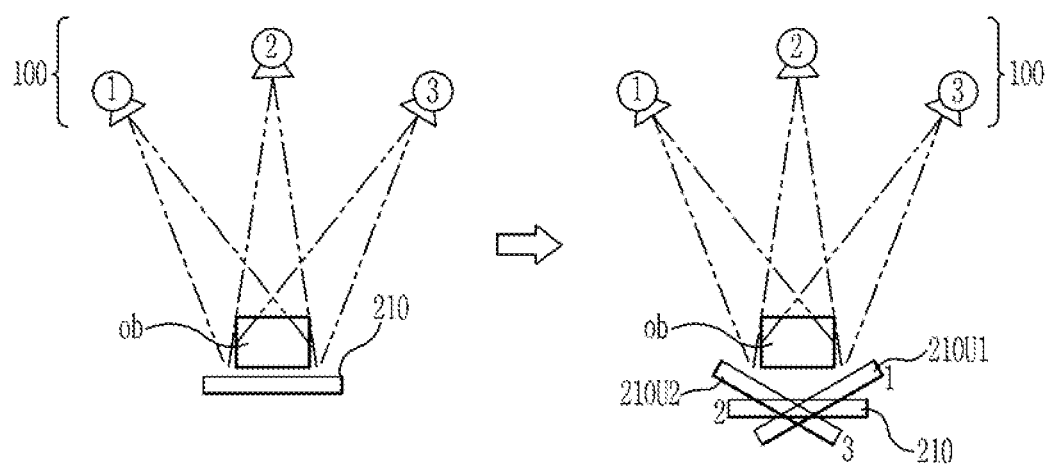
FIG. 13 is a view which illustrates a process for generating a full isocentric X-ray image, according to an exemplary embodiment.

FIG. 13 is a view which illustrates a process for generating a full isocentric X-ray image, according to an exemplary embodiment. FIG. 14 is a flowchart which illustrates a process for generating a full isocentric X-ray image, according to an exemplary embodiment. FIG. 15 is a view which illustrates a process for generating a full isocentric X-ray image, according to another exemplary embodiment.

With reference to FIG. 13, in a case in which the X-ray emitter 100 irradiates an object ob with X-rays at a plurality of original X-ray emission positions, when the X-ray emitter 100 emits X-rays in a lateral direction (e.g., when the X-ray emitter 100 is located at position 1 or position 3) in a fixed state of the X-ray detection panel 210, distortion occurs in an X-ray image.

Thus, if it is impossible to rotate the X-ray detection panel 210, the distortion of the X-ray image needs to be corrected.

In particular, as illustrated in FIG. 13, when the X-ray emitter 100 irradiates the object ob with X-rays at an X-ray imaging position, e.g., at position 1, a full isocentric X-ray image may be generated by correcting the X-ray image as if an X-ray image is acquired by receiving and detecting the emitted X-rays using the X-ray detection panel 210 located at a position 210U1 which corresponds to the position 1.

Figure 14:
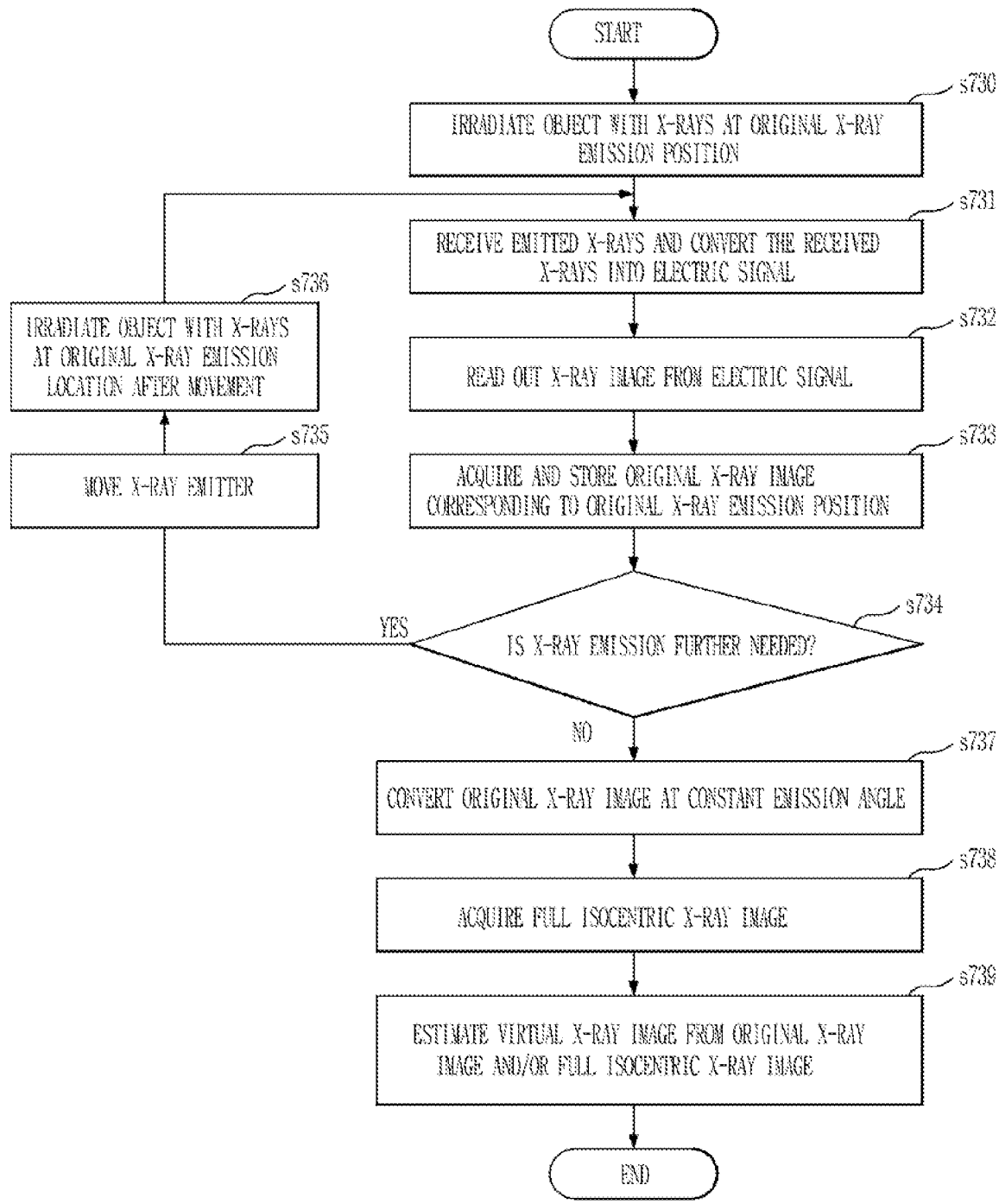
FIG. 14 is a flowchart which illustrates a process for generating a full isocentric X-ray image, according to an exemplary embodiment.

Referring to FIG. 14, the process for acquiring a full isocentric X-ray image, according to an exemplary embodiment, includes irradiating an object with X-rays at a predetermined original X-ray emission position in operation s730, receiving the emitted X-rays and converting the received X-rays into an electric signal in operation s731, reading an X-ray image out of the electric signal in operation s732, and acquiring an original X-ray image which corresponds to the original X-ray emission position and storing the original X-ray image in a storage unit 410 in operation s733.

If further X-ray emission is needed as determined in operation s734, the X-ray emitter 100 may be moved in operation s735, the object may be irradiated with X-rays at a post-movement position in operation s736, and operations s731, s732, and s733 may be repeated as desired, thereby acquiring a plurality of original X-ray images.

When a determination is made in operation s734 that there is no need for additional original X-ray images, in operation s737, X-ray images which are captured at a constant emission angle from among the acquired original X-ray images are converted based on a transformation formula by using a location of the X-ray emitter 100, a location of the X-ray detector 200, in particular, the X-ray detection panel 210, X-ray emission angles, and/or the like, thereby facilitating a generation of a full isocentric X-ray image in operation s738. Then, in operation s739, a virtual X-ray image is estimated by using the original X-ray images and/or the full isocentric X-ray image.

A method for generating a full isocentric X-ray image will now be described in more detail with reference to FIG. 15.

Figure 15:
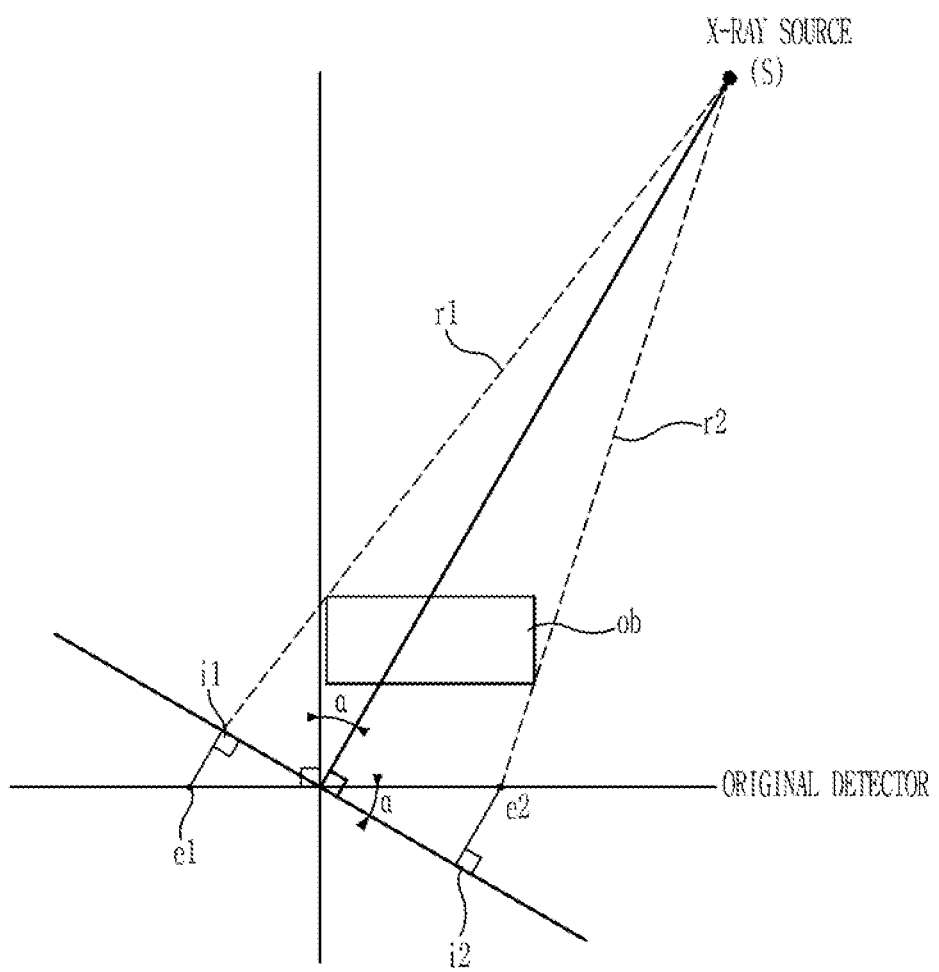
FIG. 15 is a view which illustrates a process for generating a full isocentric X-ray image, according to another exemplary embodiment.

In FIG. 15, the X-ray emitter 100, which is an X-ray source S which is configured to generate X-rays and irradiate an object ob with the generated X-rays, is illustrated. In the drawing, an x-axis denotes a fixed position of the X-ray detector 200, i.e., an original X-ray detector 200, and a segment between the X-ray source S and the origin and a y-axis have a predetermined emission angle α therebetween.

When the X-ray source S irradiates the object ob with X-rays, X-rays r1 and r2 at opposite limits of an X-ray emission range reach two points of the original X-ray detector 200, i.e., point e1 and point e2.

In this case, it may be assumed that a virtual X-ray detector is representable as a segment that is perpendicular to the segment between the X-ray source S and the origin and passes through the origin. In this regard, with reference to FIG. 15, it may be easily confirmed that the original X-ray detector 200 and the virtual X-ray detector have the same angle therebetween as the predetermined emission angle α.

Points at which the virtual X-ray detector and segments that pass through the points e1 and e2 at which the X-rays are received and are perpendicular to the virtual X-ray detector intersect each other are denoted as i1 and i2, respectively.

In this regard, an equation which may be used for performing a conversion of e1 to i1 and e2 to i2 may be applied to the acquired X-ray images in order to generate a full isocentric X-ray image which corresponds to an X-ray image which would be acquired by receiving X-rays from the X-ray source S in a vertical direction while the X-ray detector 200 constantly rotates.

Accordingly, distortion of X-ray images due to emission angles of the X-ray emitter 100 may be corrected, and an X-ray image which could be acquired by detecting X-rays while the X-ray detector 200 virtually rotates without physical rotation may be generated.

To calculate the full isocentric X-ray image, the full isocentric image processing unit 340 obtains the equation for conversion of e1 to i1 and e2 to i2 by using a location of the X-ray emitter 100, a location of the X-ray detector 200, in particular, the X-ray detection panel 210, X-ray emission angles, and/or the like, and applies the equation to an X-ray image which is acquired in a fixed state of the X-ray detector 200 in order to generate the full isocentric X-ray image.

Hereinafter, an X-ray image acquisition method according to another exemplary embodiment will be described with reference to FIG. 16.

Figure 16:
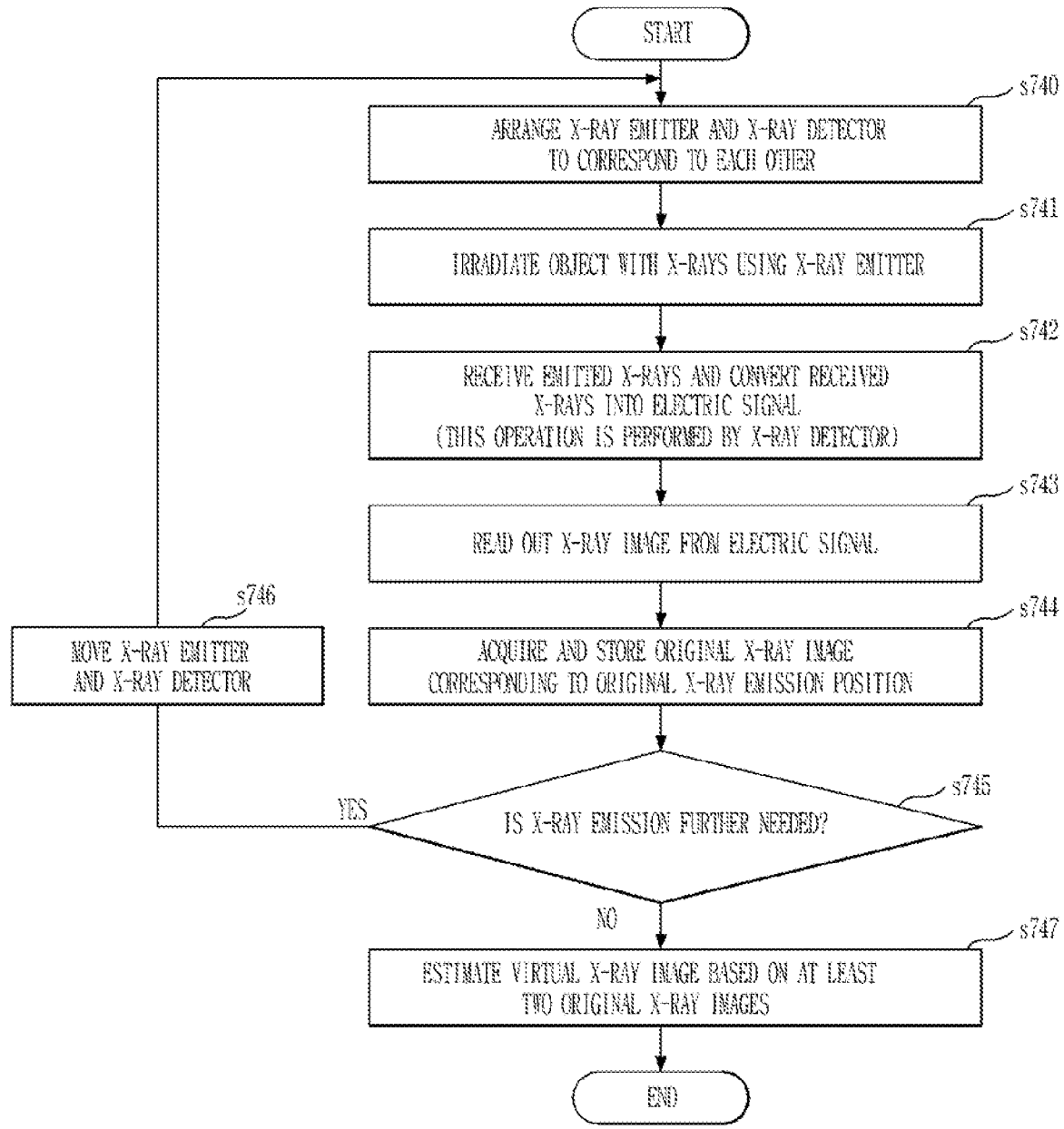
FIG. 16 is a flowchart which illustrates a method for acquiring an X-ray image, according to another exemplary embodiment.

FIG. 16 is a flowchart which illustrates a method for acquiring an X-ray image, according to another exemplary embodiment.

The X-ray image processing method performed using the X-ray imaging apparatus in a state in which a plurality of X-ray emitters 100 are used or the X-ray emitter 100 is moved and the X-ray detector 200 is in a fixed state has already been described.

According to an exemplary embodiment, as illustrated in FIG. 5, the X-ray image processing method may be performed by using the X-ray imaging apparatus in which the X-ray detector 200, in particular, the X-ray detection panel 210, is moved while drawing an arc about the central point a.

In particular, according to an exemplary embodiment, as illustrated in FIG. 16, first, in operation s740, the X-ray emitter 100 and the X-ray detector 200 are arranged to correspond to each other. In this regard, as described above, a position in which the X-ray emitter 100 is located is denoted as an original X-ray emission location. Such disposition may be performed by receiving a control command from the controller 400 based on an input by a user or a pre-stored setting.

Then, in operation s741, the X-ray emitter 100 irradiates an object ob with X-rays, and in operation s742, the X-ray detector 200 receives the emitted X-rays and converts the received X-rays into an electric signal. In operation s743, the image processor 300 reads out an X-ray image from the electric signal which is output from the X-ray detector 200. Accordingly, in operation s744, an original X-ray image which corresponds to the original X-ray emission location is acquired and stored in the storage unit 410.

If an X-ray image further needs to be acquired as determined in operation s745, the X-ray emitter 100 is moved along with the X-ray detector 200 in operation s746. In this case, even though the X-ray detector 200 is moved, the object ob is in a fixed state. Therefore, X-ray imaging may be performed on the object ob at various angles.

The moved X-ray emitter 100 and the X-ray detector 200 are arranged to correspond to each other as described above in operation s740, and the object ob is irradiated again with X-rays in order to acquire another original X-ray image which corresponds to another original X-ray emission location.

Thereafter, when a determination is made in operation s745 that there is no need for additional original X-ray image, virtual X-ray images (e.g., U1 and the like) may be estimated in operation s747 based on at least two original X-ray images (e.g., first and second original X-ray images O1 and O2) using the above-described method and thereby generated.

Figure 17:
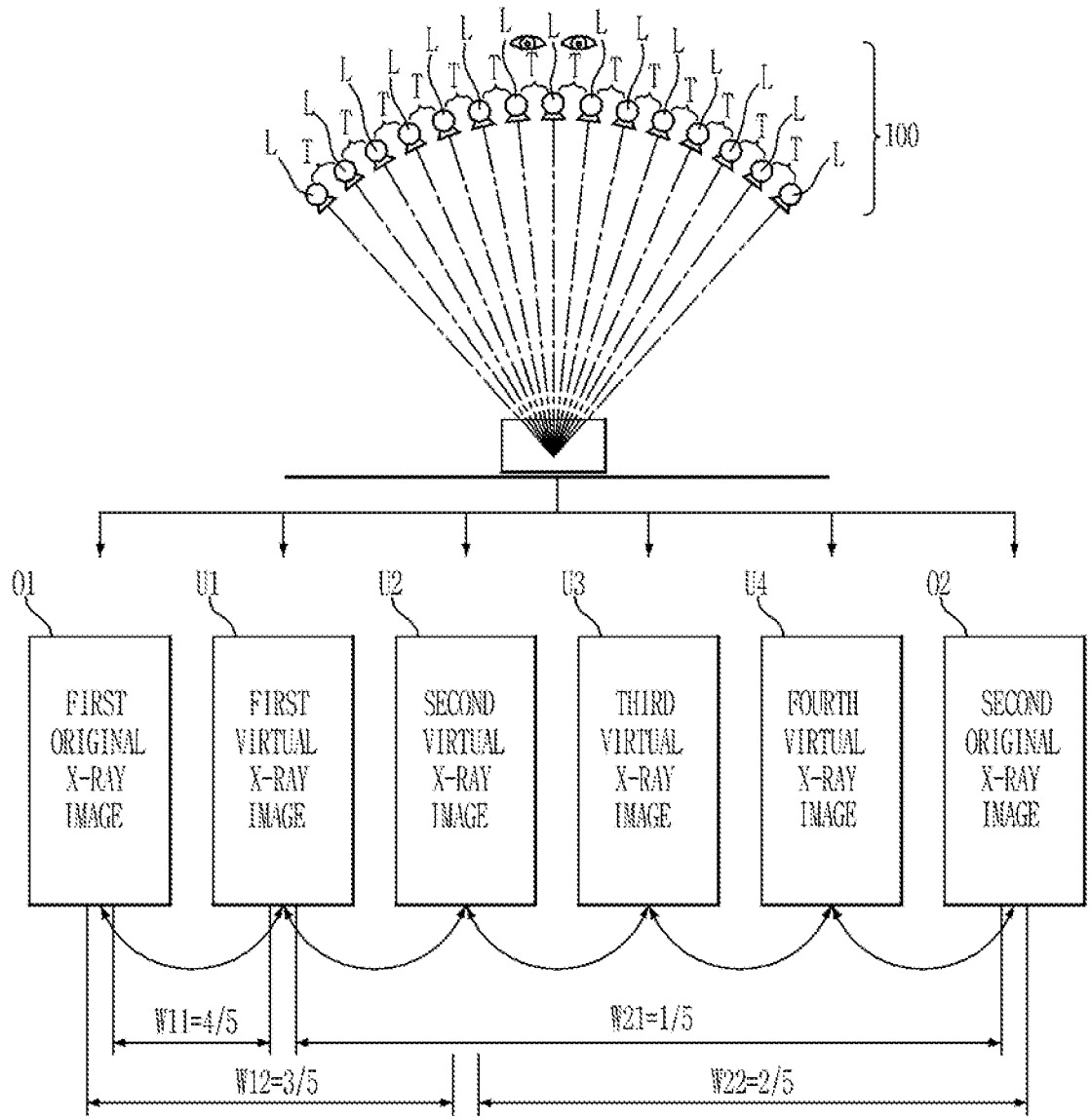
FIG. 17 is a view which illustrates acquired virtual X-ray images, according to an exemplary embodiment.

FIG. 17 is a view which illustrates generated virtual X-ray images, according to an exemplary embodiment.

As illustrated in FIG. 17, a plurality of original X-ray images (e.g., O1 and O2) of an object ob at various angles which correspond to a plurality of original X-ray emission locations L and a plurality of virtual X-ray images (e.g., U1, U2, U3, and U4) which correspond to a plurality of virtual X-ray emission locations T between the original X-ray emission locations L may be generated by executing the above-described method.

In this regard, the number of the original X-ray emission locations L, i.e., the number of locations at which X-rays are emitted, may be determined by user selection, and the number of the virtual X-ray emission locations T between the original X-ray emission locations L may also be determined by user selection.

Hereinafter, a process for generating a stereoscopic image by using original X-ray images and generated virtual X-ray images will be described with reference to FIG. 18 and FIG. 19.

Figure 18:
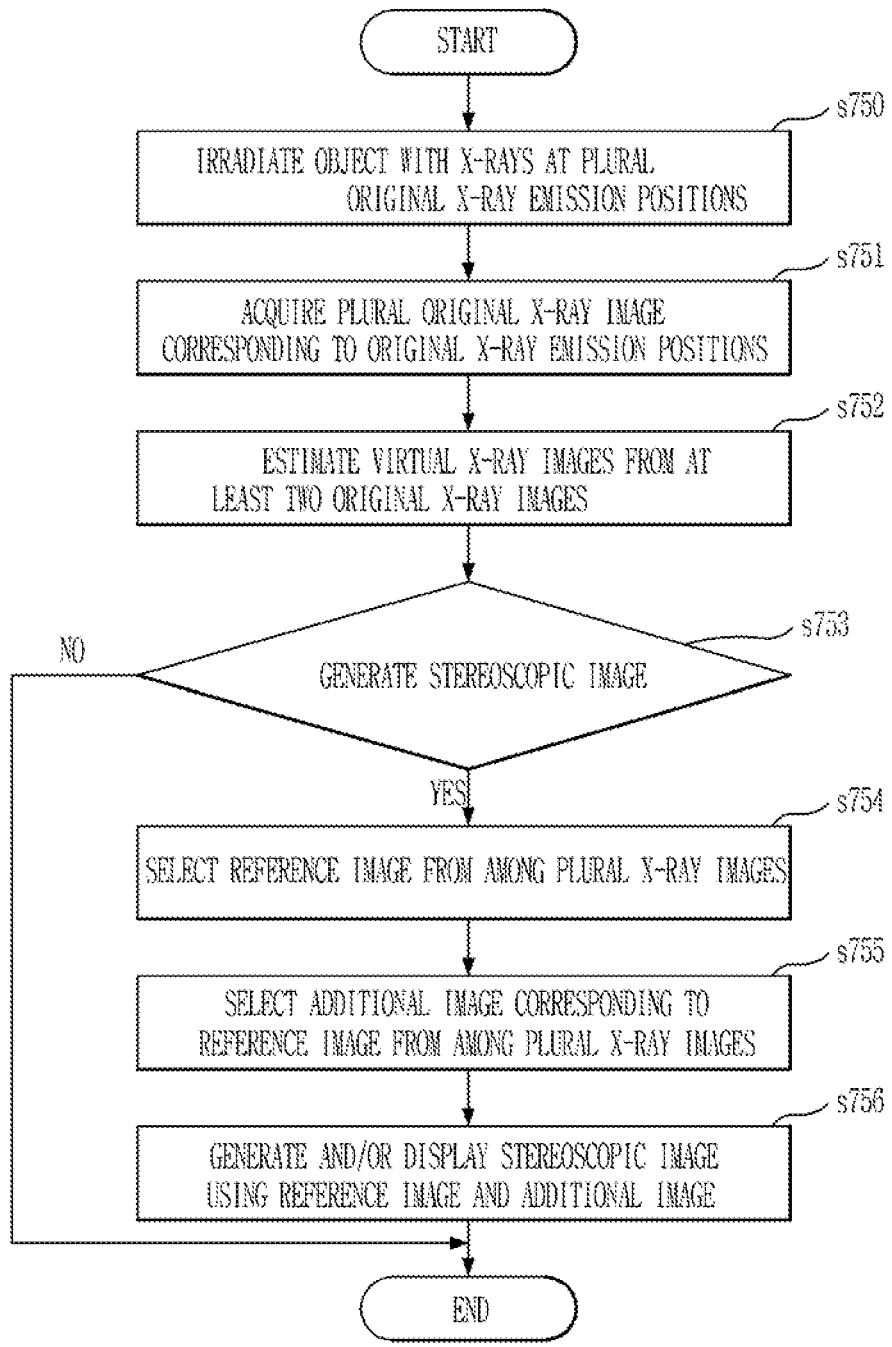
FIG. 18 is a flowchart which illustrates a process for generating a stereoscopic image by using original X-ray images and acquired virtual X-ray images, according to an exemplary embodiment.
Figure 19:
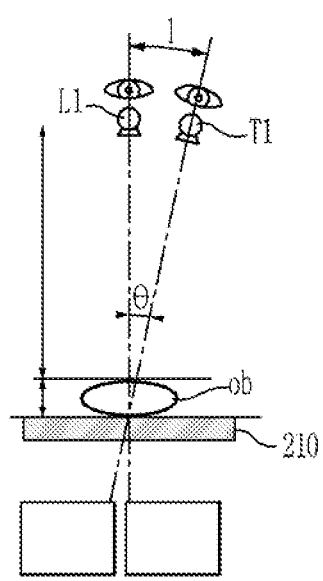
FIG. 19 is a view which illustrates a process for generating a stereoscopic image by using original X-ray images and acquired virtual X-ray images, according to an exemplary embodiment.

FIG. 18 is a flowchart which illustrates a process for generating a stereoscopic image by using original X-ray images and generated virtual X-ray images, according to an exemplary embodiment. FIG. 19 is a view which illustrates a process for generating a stereoscopic image by using original X-ray images and generated virtual X-ray images, according to an exemplary embodiment.

According to an exemplary embodiment, as illustrated in FIG. 18, first, in operation s750, an object ob is irradiated with X-rays at a plurality of original X-ray emission locations as described above, a plurality of original X-ray images corresponding to the original X-ray emission locations are acquired in operation s751, and a plurality of virtual X-ray images are estimated from at least two of the original X-ray images and thereby generated in operation s752.

If a stereoscopic image is generated based on an operation by a user or a pre-stored setting, or the acquired X-ray image is displayed as a stereoscopic image on the display unit 500, as determined in operation s753, a reference X-ray image is selected from among the original X-ray images and the virtual X-ray images in operation s754. An X-ray image selected as the reference X-ray image may be any of an original X-ray image L or a virtual X-ray image T.

Subsequently, in operation s755, an additional X-ray image which corresponds to to the reference X-ray image is selected from among the original X-ray images and the virtual X-ray images.

As described above, a stereoscopic image uses binocular parallax. In particular, referring to FIG. 19, the eyes of a human are spaced apart from each other by a certain distance I, and thus, a slight difference between an image seen by the left eye and an image seen by the right eye occurs when an object ob is viewed. In this aspect, the images seen by the right and left eyes for the object ob viewed at different angles are different by an angle 8 between the object ob and the respective eyes. A human brain senses such a difference, and thus, the object ob is stereoscopically viewed.

Similarly, according to an exemplary embodiment, any one of an original X-ray image L1 and a virtual X-ray image T1 of the object ob is selected as a reference X-ray image corresponding to a left eye or a right eye, and any one of the original X-ray image L1 and the virtual X-ray image T1 is selected as an additional X-ray image corresponding to the right eye or the left eye, whereby the object ob, such as the human body is stereoscopically viewed.

In this case, according to an exemplary embodiment, an X-ray image selected as the reference X-ray image and an X-ray image selected as the additional X-ray image may be adjacent X-ray images, i.e., adjacent X-ray images selected from among original X-ray images and virtual X-ray images.

When the reference X-ray image and the additional X-ray image are selected, a separate stereoscopic image may be generated by using the reference X-ray image and the additional X-ray image (e.g., a red-and-blue glasses method), the reference X-ray image and the additional X-ray image may be repeatedly displayed at time intervals (e.g., a shutter glasses method), or the reference X-ray image and the additional X-ray image may be may be displayed on different monitors, whereby an X-ray image for the object ob may be stereoscopically viewed by a user.

The process for generating a stereoscopic image may be performed by the stereoscopic image processor 360, and the stereoscopic image processor 360 generates a separate stereoscopic X-ray image by using the selected reference X-ray image and the additional X-ray image by using a stereoscopic image generation and display method, e.g., a glasses method or a non-glasses method, or displays the selected reference X-ray image and the additional X-ray image on the display unit 500.

Hereinafter, a process for generating a multi-view image by using original X-ray images and generated virtual X-ray images will be described.

Figure 20:
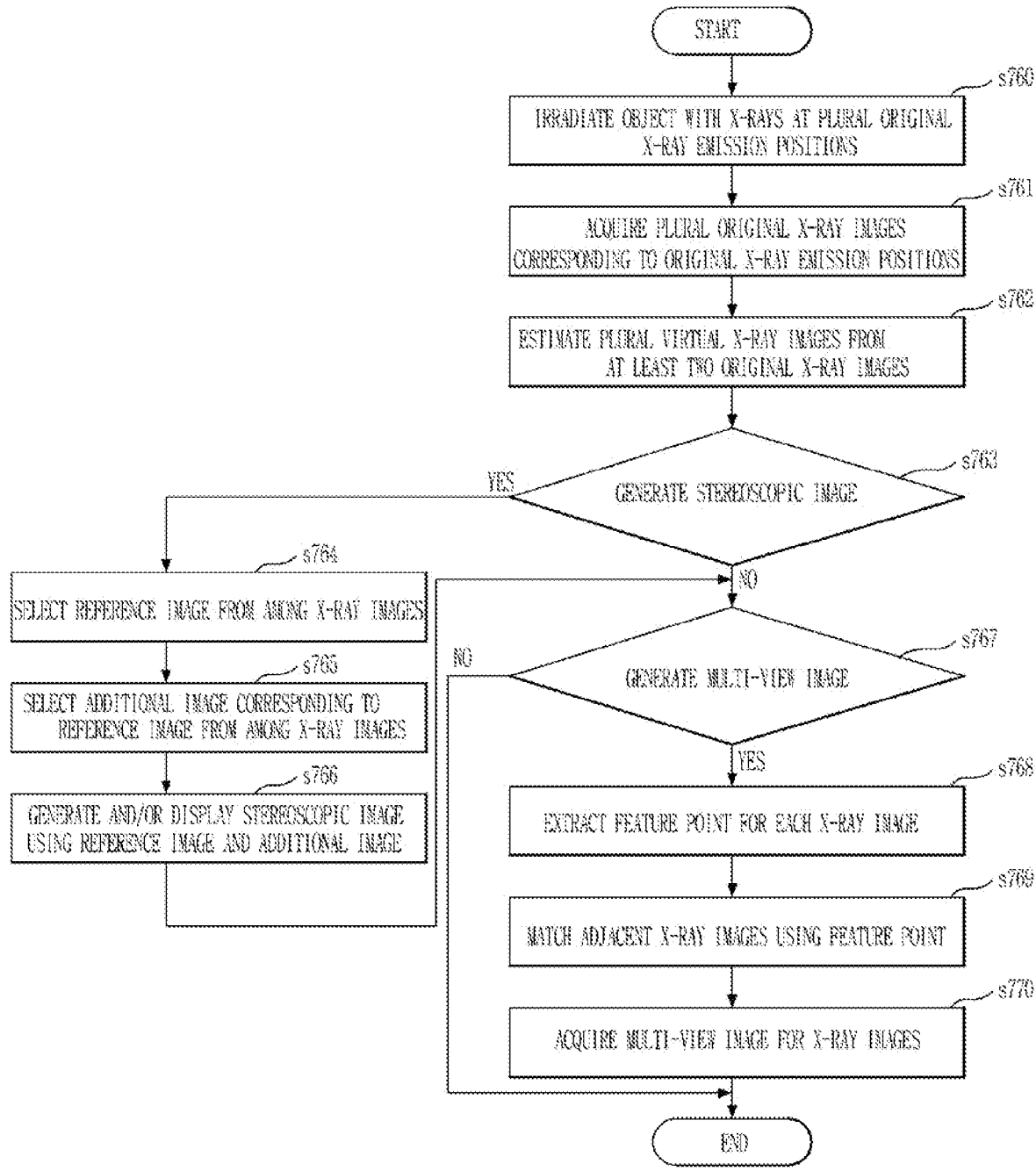
FIG. 20 is a flowchart which illustrates a process for generating a multi-view image by using original X-ray images and acquired virtual X-ray images, according to an exemplary embodiment.
Figure 21:
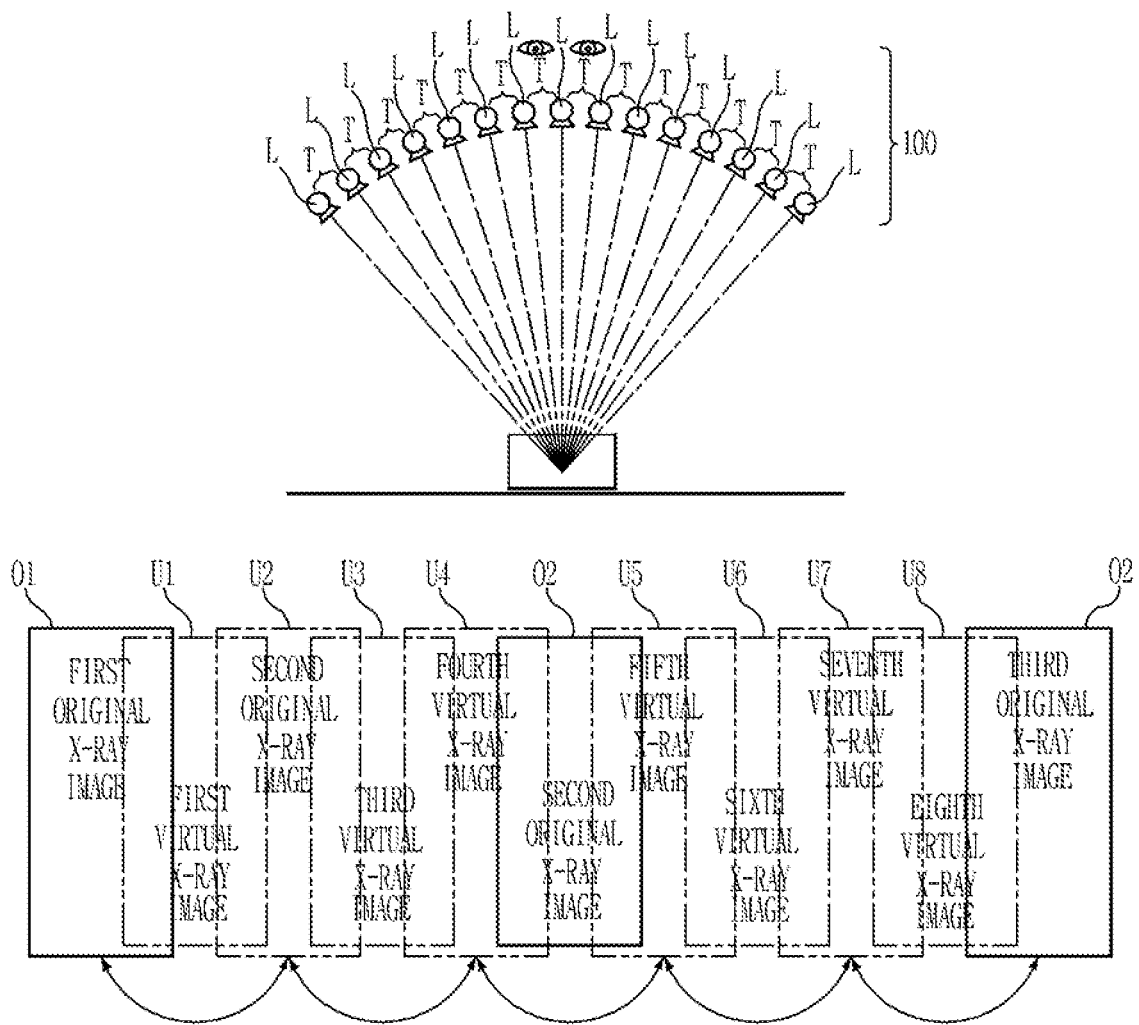
FIG. 21 is a view which illustrates a process for generating a multi-view image by using original X-ray images and acquired virtual X-ray images, according to an exemplary embodiment.

FIG. 20 is a flowchart which illustrates a process for generating a multi-view image by using original X-ray images and generated virtual X-ray images, according to an exemplary embodiment. FIG. 21 is a view which illustrates a process for generating a multi-view image by using original X-ray images and generated virtual X-ray images, according to an exemplary embodiment.

According to an exemplary embodiment, as illustrated in FIG. 20, first, in operation s760, an object ob is irradiated with X-rays at a plurality of original X-ray emission locations, a plurality of original X-ray images which correspond to the original X-ray emission locations are acquired in operation s761, and then a plurality of virtual X-ray images are estimated and acquired from at least two of the original X-ray images in operation s762.

Although not shown, in this case, the original X-ray images at the original X-ray emission locations may be acquired by using the X-ray emitter 100 that is movable or a plurality of X-ray emitters 100, and the virtual X-ray images may be generated therefrom.

According to an exemplary embodiment, the original X-ray images and the virtual X-ray images may be acquired and then, in operation s763, a stereoscopic image may be generated by using the original X-ray images and the virtual X-ray images.

In this case, as described above, at least one reference X-ray image is selected from among the original and virtual X-ray images in operation s764, at least one additional X-ray image which corresponds to the at least one reference X-ray image is selected from among the original and virtual X-ray images in operation s765, and in operation s766, a stereoscopic X-ray image is generated by using the reference X-ray image and the additional X-ray image, or the reference X-ray image and the additional X-ray image are stereoscopically displayed on the display unit 500.

According to an exemplary embodiment, after or without generation of the stereoscopic X-ray image, in operation s767, a multi-view image may be generated.

For the generation of the multi-view image, in operation s768, feature points are extracted from two X-ray images at adjacent X-ray emission locations, which are selected from among the original X-ray images or the virtual X-ray images. In this regard, the feature points may be characteristic points that correspond to each other in the two X-ray images and are distinguishable from other structures inside the two X-ray images, e.g., lesions or the like. According to exemplary embodiments, the stereoscopic X-ray image which is generated by using the above-described method may be used instead of the original or virtual X-ray images.

Thereafter, in operation s769, the adjacent X-ray images are matched by using the extracted feature points.

Matching of the adjacent X-ray images using the feature points is performed on all or some of the original X-ray images and the virtual X-ray images in order to generate a multi-view image for the X-ray images in operation s770.

As a result, as illustrated in FIG. 21, a multi-view image in which a plurality of original X-ray images, e.g., first, second, and third original X-ray images O1, O2, and O3, may be acquired, and a plurality of virtual X-ray images, e.g., first virtual X-ray image U1, second virtual X-ray image U2, third virtual X-ray image U3, fourth virtual X-ray image U4, fifth virtual X-ray image U5, sixth virtual X-ray image U6, seventh virtual X-ray image U7, and eighth virtual X-ray image U8, which are connected to each other, may be generated.

Accordingly, a user may view the object ob at various angles. When stereoscopic X-ray images are used in image matching, a user may stereoscopically view the object ob at various angles. Accordingly, a high efficiency in determination for inner tissues of the object ob, e.g., diagnosis or the like for lesions inside the object ob, may be obtained.

Hereinafter, X-ray imaging apparatuses according to various exemplary embodiments will be described with reference to FIGS. 22A, 22B, 22C, 23A, and 23B.

Figure 22A:
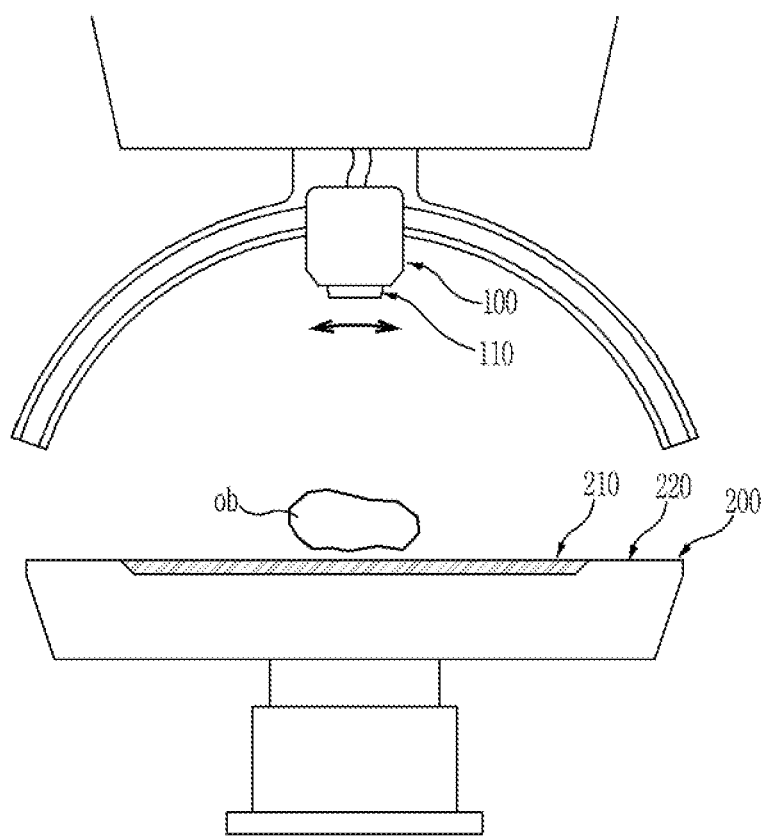
FIG. 22A is a front view of an X-ray imaging apparatus, according to an exemplary embodiment.

FIG. 22A is a front view of an X-ray imaging apparatus, according to an exemplary embodiment.

As illustrated in FIG. 22A, according to an exemplary embodiment, the X-ray imaging apparatus may include: a table 220 on which an object ob is placed and that includes an X-ray detection panel 210; and an X-ray emitter 100 which is disposed above the table 220 and movable in a particular direction.

In this regard, the X-ray emitter 100 may be connected to a separate moving member 110, e.g., rails or the like, so as to be movable with respect to the moving member 110 to each of a plurality of original X-ray emission positions.

The X-ray emitter 100 may be moved by the moving member 110 while drawing an arc about a predetermined origin, e.g., a certain point inside the object ob.

When the X-ray emitter 100 irradiates the object ob with X-rays at each of the plurality of original X-ray emission positions while in motion, the X-ray detection panel 210 receives the emitted X-rays and converts the received X-rays into an electric signal. Then, an image processor which is installed in the table 220 or an image processor of an information processing apparatus, such as a computer or the like, which is externally connected to the table 220, reads out an original X-ray image from the electric signal, and a virtual X-ray image is generated from the read-out original X-ray image. In addition, according to exemplary embodiments, a stereoscopic X-ray image and/or a multi-view image may be generated from original X-ray images and virtual X-ray images and displayed to a user.

Figure 22B:
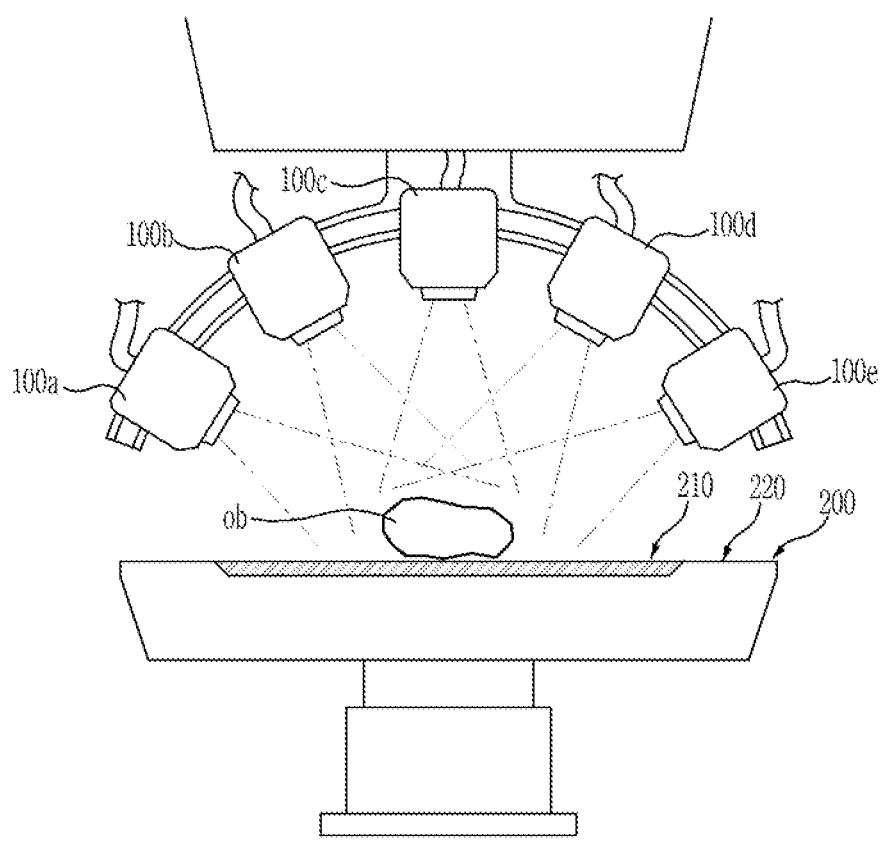
FIG. 22B is a front view of an X-ray imaging apparatus, according to another exemplary embodiment.

FIG. 22B is a front view of an X-ray imaging apparatus, according to another exemplary embodiment.

As illustrated in FIG. 22B, the X-ray imaging apparatus according to another exemplary embodiment may include a plurality of X-ray emitters 100a, 100b, 100c, 100d, and 100e. The X-ray emitters 100a, 100b, 100c, 100d, and 100e may be controlled in accordance with an operation by a user and/or a pre-stored setting in order to irradiate the object ob with X-rays at each of a plurality of different original X-ray emission locations.

In this case, the X-ray emitters 100a, 100b, 100c, 100d, and 100e may be configured to sequentially irradiate the object ob with X-rays in a certain order.

In addition, according to exemplary embodiments, the X-ray emitters 100a, 100b, 100c, 100d, and 100e may be movable in a particular direction. In this case, the object ob may be irradiated with X-rays at a greater number of the original X-ray emission locations than in a case in which the X-ray emitters 100a, 100b, 100c, 100d, and 100e are not movable, and thus, a greater number of different original X-ray images may be acquired.

Similarly as described above, the X-ray imaging apparatus illustrated in FIG. 22B may also estimate and acquire at least one virtual X-ray image from a plurality of original X-ray images, and may generate a stereoscopic X-ray image, a multi-view image, and/or a multi-view image which is displayable as a stereoscopic image from the original X-ray images and the at least one virtual X-ray image.

Figure 22C:
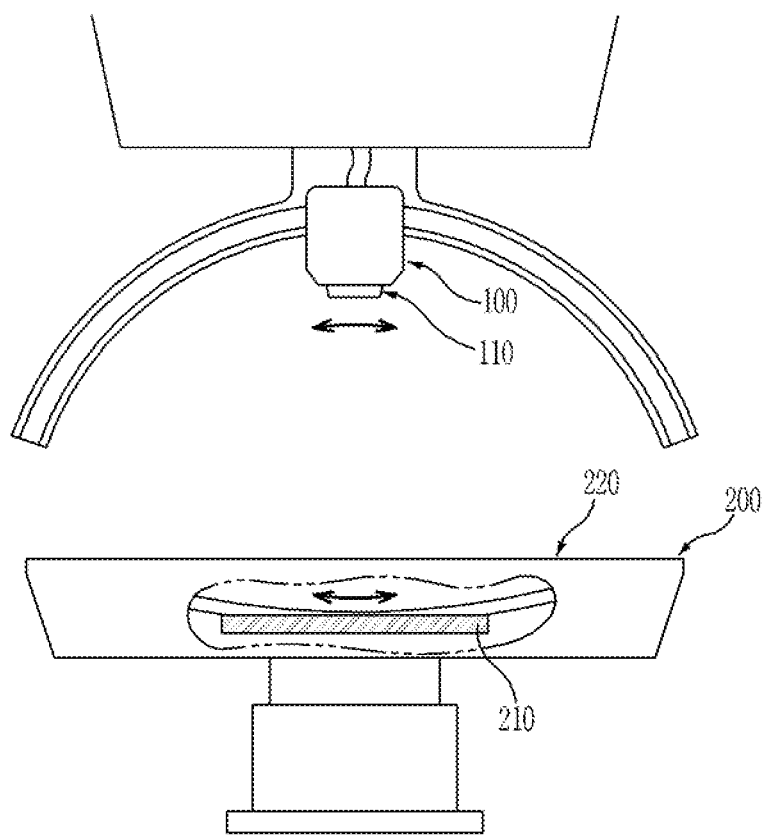
FIG. 22C is a front view of an X-ray imaging apparatus, according to another exemplary embodiment.

FIG. 22C is a front view of an X-ray imaging apparatus, according to another exemplary embodiment.

As illustrated in FIG. 22C, the X-ray imaging apparatus according to another exemplary embodiment may include a table 220 which is configured to support an object ob and an X-ray detection panel 210 which is disposed in the table 220 and movable in a particular direction, e.g., in left and right directions of FIG. 22C. In addition, the X-ray imaging apparatus may include an X-ray emitter 100 which is disposed above the table 220 and movable in a certain direction.

In this regard, the X-ray emitter 100 and/or the X-ray detection panel 210 may be coupled to a separate moving member 110, e.g., rails or the like, so that the X-ray emitter 100 and/or the X-ray detection panel 210 is movable.

The X-ray emitter 100 and the X-ray detection panel 210 may be moved by the moving member 110 while drawing an arc about a predetermined origin, e.g., a certain point inside the object ob.

In addition, the X-ray emitter 100 and the X-ray detection panel 210 may be controlled to be moved while facing each other in order to facilitate a detection of X-rays emitted from the X-ray emitter 100.

The X-ray emitter 100 and the X-ray detection panel 210 are moved together, and thus, the X-ray imaging apparatus as illustrated in FIG. 22C may acquire a plurality of original X-ray images that are not distorted, without a need for performing a process for generating a full isocentric X-ray image.

In addition, similarly as described above, the X-ray imaging apparatus illustrated in FIG. 22C may also estimate and acquire at least one virtual X-ray image from a plurality of original X-ray images, and may generate a stereoscopic X-ray image, a multi-view image, and/or a multi-view image which is displayable as a stereoscopic image from the original X-ray images and the at least one virtual X-ray image.

Figure 23A:
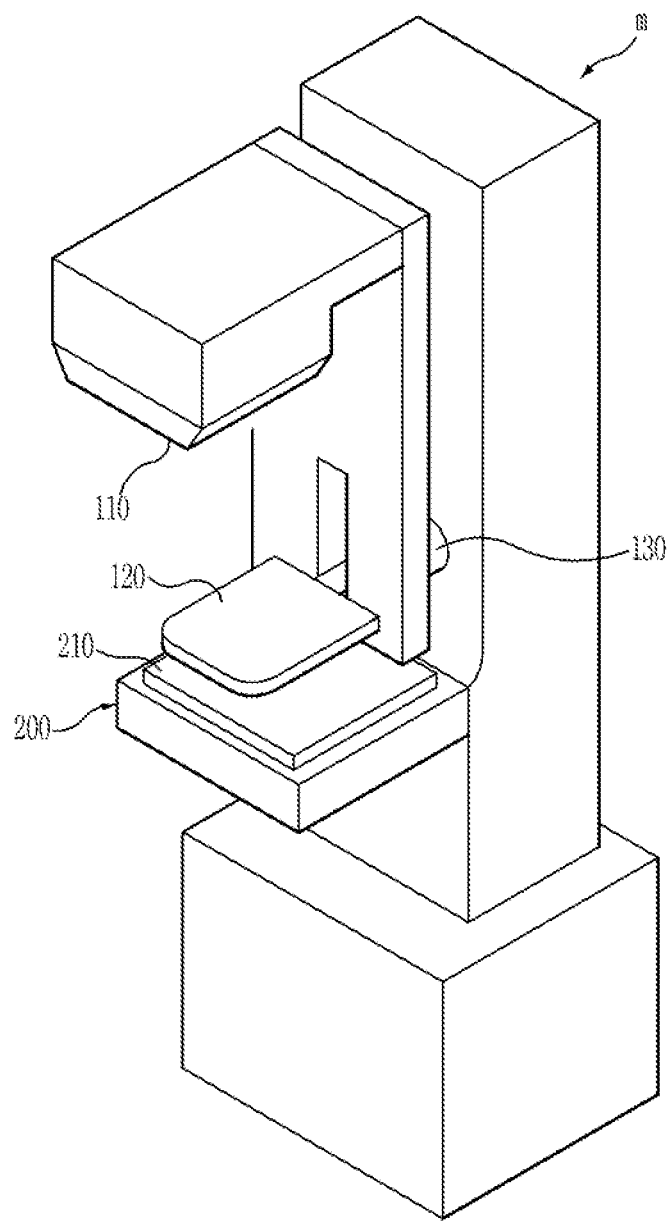
FIG. 23A is a perspective view of an X-ray imaging apparatus, in particular, a mammography apparatus, according to an exemplary embodiment.

FIG. 23A is a perspective view of an X-ray imaging apparatus, in particular, a mammography apparatus, according to an exemplary embodiment.

As illustrated in FIG. 23A, the X-ray imaging apparatus may be a mammography apparatus m.

An X-ray emitter 100 of the mammography apparatus m may also be moved while drawing a constant arc about a predetermined origin as described above.

According to an exemplary embodiment, the X-ray emitter 100 may be connected to a predetermined movement control unit 130, and thus be rotatably moved about the movement control unit 130 as a rotation axis.

In this case, the movement control unit 130 may simultaneously or sequentially rotate the X-ray emitter 100 and the X-ray detector 200 so that the X-ray emitter 100 and the X-ray detector 200, in particular, the X-ray detection panel 210, face each other.

In addition, as illustrated in FIG. 23A, the movement control unit 130 may be disposed between the X-ray emitter 100 and the X-ray detector 200.

The X-ray emitter 100 of the mammography apparatus m is rotatably movable by using the movement control unit 130, and thus, a plurality of original X-ray images at various angles may be acquired by performing X-ray imaging of a breast which is compressed by a compressor 120.

In addition, as described above, the mammography apparatus of FIG. 23A may also estimate and acquire at least one virtual X-ray image from a plurality of original X-ray images, and may generate a stereoscopic X-ray image, a multi-view image, and/or a multi-view image which is displayable as a stereoscopic image from the original X-ray images and the at least one virtual X-ray image.

In addition, according to another exemplary embodiment, the X-ray detection panel 210 may be installed in the table 220 of the mammography apparatus, and the X-ray detection panel 210 may be moved while drawing a constant arc.

Figure 23B:
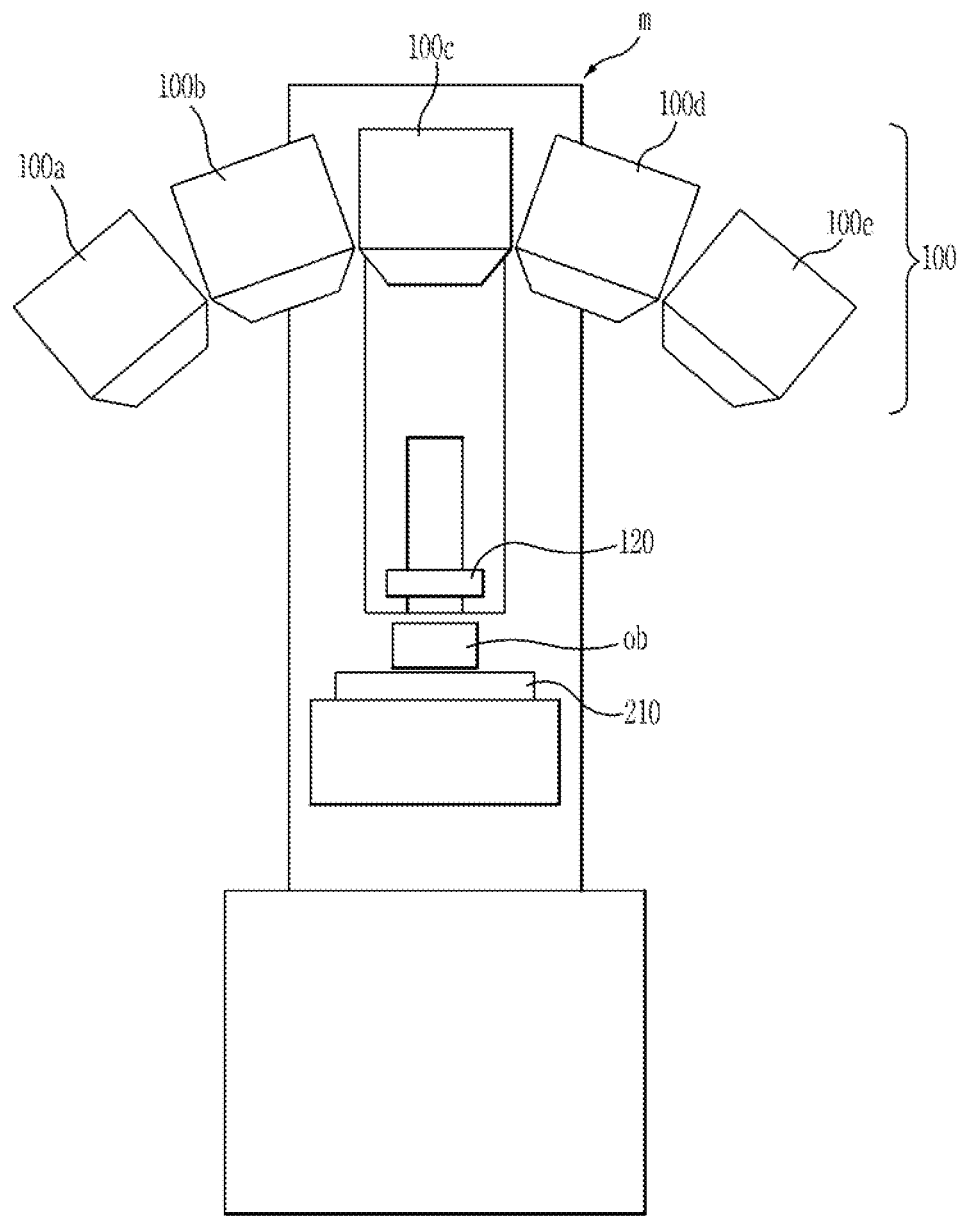
FIG. 23B is a front view of a mammography apparatus, according to another exemplary embodiment.

FIG. 23B is a front view of a mammography apparatus, according to another exemplary embodiment.

As illustrated in FIG. 23B, the mammography apparatus m according to another exemplary embodiment may include a plurality of X-ray emitters 100a, 100b, 100c, 100d, and 100e, and the X-ray emitters 100a, 100b, 100c, 100d, and 100e may be controlled in accordance with an operation by a user and/or a pre-stored setting in order to irradiate an object ob with X-rays at each of a plurality of different original X-ray emission positions.

In addition, according to exemplary embodiments, the X-ray emitters 100a, 100b, 100c, 100d, and 100e of the mammography apparatus m may be movable in a certain direction. In this case, as described above, a greater number of different original X-ray images may be acquired.

Similarly, the mammography apparatus m as illustrated in FIG. 23B may also generate at least one virtual X-ray image by estimating from a plurality of original X-ray images, and may generate a stereoscopic X-ray image, a multi-view image, and/or a multi-view image which is displayable as a stereoscopic image from the original X-ray images and the at least one virtual X-ray image.

As is apparent from the above description, according to an X-ray imaging apparatus and an X-ray image processing method, a greater number of X-ray images at various X-ray emission positions may be generated by using a relatively small number of X-ray images which are captured at a correspondingly small number of X-ray emission positions.

Accordingly, a plurality of stereoscopic X-ray images and/or a multi-view image which includes views of the object from any one or more of various angles may be acquired by performing a relatively small number of X-ray imaging processes.

In addition, a continuous stereoscopic X-ray image may also be displayed by using a relatively small number of X-ray images.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An X-ray imaging apparatus comprising:
   at least one X-ray emitter which is configured to irradiate an object with X-rays at a plurality of X-ray emission positions;
   an X-ray detector which is configured to detect X-rays which have been emitted by the at least one X-ray emitter and propagated through the object, and to convert the detected X-rays into an electric signal; and
   an image processor which is configured to acquire a plurality of original X-ray images which respectively correspond to the plurality of X-ray emission positions from the generated electric signal, and to estimate a virtual X-ray image which is acquirable at an additional X-ray emission position which is located between at least two of the plurality of X-ray emission positions, based on at least two of the plurality of original X-ray images.

2. The X-ray imaging apparatus according to claim 1, wherein the at least one X-ray emitter is movable to each of the plurality of X-ray emission positions in order to irradiate the object with X-rays at each of the plurality of X-ray emission positions.

3. The X-ray imaging apparatus according to claim 1, wherein the image processor is further configured to generate a stereoscopic X-ray image which is based on two X-ray images from among the plurality of original X-ray images and the estimated virtual X-ray image, which two X-ray images correspond to adjacent X-ray emission positions, and to display the generated stereoscopic X-ray image.

4. The X-ray imaging apparatus according to claim 1, wherein the image processor is further configured to generate a multi-view image of the object which includes views which correspond to at least two angles by matching two X-ray images from among the plurality of original X-ray images and the estimated virtual X-ray image, which two X-ray images correspond to adjacent X-ray emission positions.

5. The X-ray imaging apparatus according to claim 1, wherein the image processor is further configured to estimate a new virtual X-ray image based on the estimated virtual X-ray image.

6. The X-ray imaging apparatus according to claim 1, wherein the image processor is further configured to convert at least one of the acquired plurality of original X-ray images in order to generate at least one full isocentric X-ray image, and to estimate the virtual X-ray image which is acquirable at the additional X-ray emission position which is located between the at least two of the plurality of X-ray emission positions, based on the at least two of the plurality of original X-ray images and the generated at least one full isocentric X-ray image.

7. The X-ray imaging apparatus according to claim 1, wherein the image processor is further configured to estimate and generate the virtual X-ray image by applying a respective weight to each of the plurality of original X-ray images based on a distance between the additional X-ray emission position at which the virtual X-ray image is acquirable and each of the X-ray emission positions which respectively correspond to the plurality of original X-ray images.

8. The X-ray imaging apparatus according to claim 1, wherein the image processor is further configured to generate the virtual X-ray image by predicting at least a partial motion of the object between at least two of the plurality of original X-ray images by using a motion prediction method, acquiring motion information which relates to the predicted at least the partial motion of the object, and estimating the virtual X-ray image based on the acquired motion information.

9. The X-ray imaging apparatus according to claim 8, wherein the image processor is further configured to predict the at least the partial motion of the object as including a linear motion.

10. The X-ray imaging apparatus according to claim 8, wherein the X-ray detector is movable to each of a plurality of light receiving positions, and wherein the X-ray detector is further configured to detect X-rays at each of the plurality of light receiving positions, and to convert the detected X-rays into at least one electric signal.

11. The X-ray imaging apparatus according to claim 8, the X-ray imaging apparatus further comprising:
   a movement controller which is configured to simultaneously or sequentially rotate the at least one X-ray emitter and the X-ray detector about a rotating shaft which is disposed between the at least one X-ray emitter and the X-ray detector such that the at least one X-ray emitter faces the X-ray detector.

12. An X-ray image processing method comprising:
   irradiating, by an X-ray emitter which is included in an X-ray imaging apparatus, an object with X-rays at a plurality of X-ray emission positions;
   receiving, by an X-ray detector which is included in the X-ray imaging apparatus, the irradiated X-rays, and converting the received X-rays into at least one electric signal;
   acquiring a plurality of original X-ray images which respectively correspond to the plurality of X-ray emission positions by reading out at least one X-ray image from the at least one electric signal; and
   estimating, based on at least two of the acquired plurality of original X-ray images, a virtual X-ray image which is acquirable at a virtual X-ray emission position which is located between the at least two X-ray emission positions which correspond to the at least two of the acquired plurality of original X-ray images.

13. The X-ray image processing method according to claim 12, wherein the irradiating comprises irradiating the object with X-rays after the X-ray emitter is moved from at least a first X-ray emission position from among the plurality of X-ray emission positions to at least a second X-ray emission position from among the plurality of X-ray emission positions.

14. The X-ray image processing method according to claim 12, further comprising simultaneously or sequentially rotating the X-ray emitter and the X-ray detector about a rotating shaft which is disposed between the X-ray emitter and the X-ray detector such that the X-ray emitter faces the X-ray detector, before the irradiating.

15. The X-ray image processing method according to claim 12, further comprising generating a stereoscopic X-ray image which is based on two X-ray images from among the plurality of original X-ray images and the estimated virtual X-ray image, which two X-ray images correspond to adjacent X-ray emission positions, and displaying the generated stereoscopic X-ray image.

16. The X-ray image processing method according to claim 12, further comprising generating a multi-view image of the object which includes views which correspond to at least two angles by matching two X-ray images from among the plurality of original X-ray images and the estimated virtual X-ray image, which two X-ray images correspond to adjacent X-ray emission positions.

17. The X-ray image processing method according to claim 12, further comprising estimating a new virtual X-ray image based on the estimated virtual X-ray image.

18. The X-ray image processing method according to claim 12, wherein the estimating comprises estimating the virtual X-ray images by applying a respective weight to each of the plurality of original X-ray images based on a distance between the virtual X-ray emission position at which the virtual X-ray image is acquirable and each of the X-ray emission positions which respectively correspond to the plurality of original X-ray images.

19. The X-ray image processing method according to claim 12, wherein the estimating comprises predicting at least a partial motion of the object between at least two of the plurality of original X-ray images by using a motion prediction method, acquiring motion information which relates to a result of the predicting, and estimating the virtual X-ray image based on the acquired motion information.

20. The X-ray image processing method according to claim 19, wherein the predicting comprises predicting the at least the partial motion of the object as including a linear motion.

* * * * *